(12) United States Patent
Carry et al.

(10) Patent No.: US 6,207,675 B1
(45) Date of Patent: Mar. 27, 2001

(54) PYRROLE DERIVATIVES, THEIR PREPARATION AND PHARMACEUTICAL COMPOSITIONS CONTAINING THEM

(75) Inventors: Jean-Christophe Carry, Meudon; Serge Mignani, Chätenay Malabry; Conception Nemecek, Thiais, all of (FR)

(73) Assignee: Rhone-Poulenc Rorer S.A., Antony (FR)

( * ) Notice: Subject to any disclaimer, the term of this patent is extended or adjusted under 35 U.S.C. 154(b) by 0 days.

(21) Appl. No.: 09/319,773

(22) PCT Filed: Dec. 10, 1997

(86) PCT No.: PCT/FR97/02248

§ 371 Date: Jun. 11, 1999

§ 102(e) Date: Jun. 11, 1999

(87) PCT Pub. No.: WO98/25925

PCT Pub. Date: Jun. 18, 1998

(30) Foreign Application Priority Data

Dec. 12, 1996 (FR) .................................................. 96 15288

(51) Int. Cl.$^7$ .......................... A61K 31/437; A61P 31/22; C07D 471/04
(52) U.S. Cl. ........................ 514/299; 546/112; 546/183
(58) Field of Search .............................. 514/299; 546/112, 546/183

(56) References Cited

U.S. PATENT DOCUMENTS 4,684,658 * 8/1987 Fabre .................................. 514/338

FOREIGN PATENT DOCUMENTS 0522944A 1/1993 (EP) .
2735476A 12/1996 (FR) .

* cited by examiner

*Primary Examiner*—Evelyn Mei Huang
(74) *Attorney, Agent, or Firm*—Finnegan, Henderson, Farabow, Garrett, Dunner, L.L.P.

(57) ABSTRACT

The invention concerns pyrrole derivatives of general formula (I) useful for treatment and prevention of diseases in which are involved viruses of the herpes family and/or cytokines in particular TNFα.

(I)

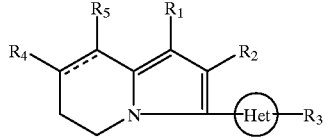

11 Claims, No Drawings

PYRROLE DERIVATIVES, THEIR PREPARATION AND PHARMACEUTICAL COMPOSITIONS CONTAINING THEM

This application is the national phase of PCT/FR97/02248, filed Dec. 10, 1997.

The present invention relates to new pyrrole derivatives of general formula:

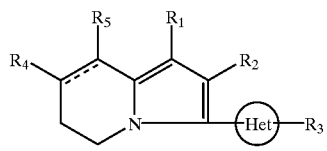

(I)

which are useful in the treatment and prevention of conditions in which viruses of the herpes family are involved, and/or in which cytokines, including $TNF_\alpha$ (Tumour Necrosis Factor alpha), are involved.

Viruses of the herpes family are responsible for numerous conditions, some of which can be very serious. It comprises in particular the group α, β and γ herpesviruses including the herpes simplex viruses 1 and 2, varicella-zoster, cytomegalovirus (CMV), herpesviruses types 6 and 7 (HHV-6 and HHV-7), Epstein-Barr virus and herpesvirus type 8 (HHV-8). The clinical forms due to a herpes simplex infection can vary from benign forms such as herpes labialis to more serious forms such as genital herpes. Herpes simplex may even be responsible for encephalitis putting the patient's life at risk. Varicella-zoster is the virus responsible for varicella and zona, it may also be responsible for more serious conditions including encephalitis. Cytomegalovirus infections are in general a symptomatic in healthy subjects, but can be the cause of morbidity [retinitis (which may lead to blindness), pneumopathies and the like] and of mortality in immunosuppressed subjects (patients suffering from AIDS or any other immunodeficiency, for example after organ transplantation or after anticancer chemotherapy). The cytomegalovirus is also responsible for severe clinical manifestations for the foetus or newborn in the case of a primary infection during pregnancy or during seropositive blood transfusion into a seronegative newborn. The herpesviruses HHV-6 and 7 are responsible for roseola and can be reactivated in immunosuppressed subjects. The HHV-8 virus is involved in Kaposi's sarcoma.

The treatments existing up until now are likely to cause serious side effects. Furthermore, for some of these viruses, the treatments can most often only be used by the intravenous route.

Cytokines (including $TNF_\alpha$) are capable of activating various viruses and/or retroviruses, for example the cytomegalovirus or the Human Immuno-deficiency Virus (HIV), and are also capable of activating cellular genes, in particular those involved in inflammatory processes, such as the genes for chemokines, cytokines and adhesion molecules.

In European Applications EP 118 321, EP 147 317 and EP 124 384 and in French Application 2 539 417, there have been described pyrrole derivatives having an antithrombotic activity or serving as intermediates for the preparation of antithrombotic derivatives. Pyrrole derivatives having an anti-TNF ativity have been described in French Application 2 735 476.

In the general formula (I), $R_1$ is a carboxamide, cycano, carboxyl, alkyloxycarbonyl, acetyl or imidazolylcarbonyl radical, $R_3$ is a hydrogen or halogen atom, or an alkyl or hydroxyl radical, and Het is a pyridyl, pyridyl N-oxide or thiazolyl radical, and a) the bond --- is a single bond, $R_2$ is a hydrogen or halogen atom, or a cyano, alkyl, al-kyloxy or trihalomethyl radical, $R_4$ is a hydrogen atom, and $R_5$ is a hydroxyl, alkyloxy, amino or haloacylamino radical, or alternatively b) the bond --- is a double bond, and $R_2$ is a hydrogen or halogen atom, or a cyano, alkyl, alkyloxy, alkenyl or trihalomethyl radical, $R_4$ is a hydrogen or halogen atom or an alkyloxy or alkylthio radical which are optionally substituted with carboxyl, alkyloxycarbonyl, amino, alkylamino or dialkylamino in which the alkyl parts can form, with the nitrogen atom to which they are attached, a 4- to 6-membered heterocycle which may, in addition, comprise another heteroatom chosen from nitrogen, oxygen or sulphur, or phthalimido, and $R_5$ is a hydrogen atom, it being understood that $R_2$ cannot be chlorine when simultaneously $R_4$ and $R_5$ are hydrogen, and when $R_1$ is cyano or carboxamido, and Het-$R_3$ is 3-pyridyl optionally substituted with fluorine at the 2 position, or alternatively when simultaneously $R_4$ is halogen, $R_5$ is hydrogen, and when $R_1$ is cyano or carboxamido and Het-$R_3$ is 3-pyridyl substituted with methyl, chlorine or fluorine at the 2 position or when $R_1$ is alkyloxycarbonyl or acetyl and when Het-$R_3$ is 3-pyridyl, the alkyl radicals being straight or branched and containing 1 to 4 carbon atoms and the acyl and alkenyl radicals being straight or branched and containing 2 to 4 carbon atoms.

According to the invention, the halogen atoms are chosen from fluorine, chlorine, bromine or iodine.

According to the invention, the heterocycles are for example chosen from the morpholine, thiomorpholine, piperidine, pyrrolidine, piperazine, N-alkylpiperazine (for example N-methylpiperazine) or azetidine ring.

According to the invention, the preparation of the products of general formula (I) is carried out by preparing a nitrile intermediate of general formula:

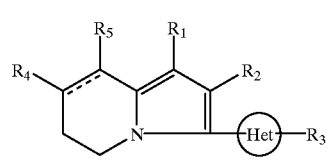

(I)

in which Het, $R_2$ and $R_3$ are defined as above, by the action of an acrylic derivative of general formula:

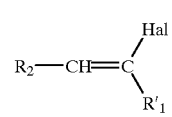

(II)

in which $R_2$ is defined as above, with the exception of representing a halogen atom, $R'_1$ is a cyano or alkyloxycarbonyl radical, and Hal is a halogen atom (for example a chlorine atom) on an acid of general formula:

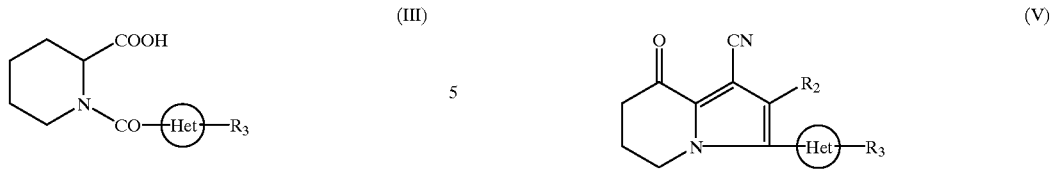

(III)

(V)

in which Het and $R_3$ are defined as above, followed by the steps of introducing the double bond and/or the radicals $R_4$ and $R_5$ and/or optionally $R_2$, and where appropriate converting the nitrile to an amide, an acid, an ester, an imidazole-containing radical or an acetyl radical, or alternatively, where appropriate, converting the ester radical to an acid, an imidazole-containing radical or an acetyl radical, by any known methods which do not alter the rest of the molecule.

By way of example, the known methods may be in particular methods described in the patent applications cited above, or the methods described in the examples which follow, or methods analogous to these methods.

The reaction of the product of general formula (II) with the acid of general formula (III) is generally carried out using the acid salt (sodium salt for example) in acetic anhydride at a temperature of between 80 and 130° C., or in para-toluenesulphonyl chloride.

When it is desired to obtain the derivative for which $R_2$ represents cyano, the product obtained is subjected to treatment with isocyanatosulphonyl chloride at a temperature of between 0 and 10° C. in an organic solvent such as acetonitrile.

When it is desired to obtain the derivative for which $R_2$ represents trihalomethyl or alkenyl, the derivative of general formula (IV) obtained is treated beforehand according to the method described in French Application 2 735 476, or by any method analogous thereto.

When it is desired to obtain the derivative of general formula (IV) for which $R_2$ represents a halogen atom, the halogenation of the intermediate of general formula (IV) for which $R_2$ is hydrogen is carried out with an N-halosuccinimide, followed by a reduction of the product obtained, for example by catalytic hydrogenation in an acidic medium, in the presence of palladium on carbon.

The halogenation is carried out with 1 or 3 equivalents of N-halosuccinimide (for example N-chlorosuccinimide). The procedure is advantageously carried out in a chlorinated solvent (dichloromethane or dichloroethane for example) or in a nitrile (acetonitrile for example) at the reflux temperature of the reaction mixture.

When it is desired to obtain a derivative as defined in a), or for which --- is a double bond and $R_4$ and $R_5$ are hydrogen atoms, the halogenation of the intermediate of general formula (IV) is carried out with an N-halosuccinimide, followed by the reduction of the product obtained, for example by catalytic hydrogenation in an acidic medium, in the presence of palladium, so as to obtain an intermediate of general formula:

in which Het, $R_2$ and $R_3$ are defined as above.

The derivative of general formula (V) can be either reduced in order to obtain a derivative for which $R_5$ is a hydroxyl radical and then, where appropriate, dehydrated in order to obtain the product for which --- is a double bond and $R_4$ and $R_5$ are hydrogen atoms, or converted to an imine and then reduced to an amine according to known methods, or treated with a trialkyl ester and then reduced, for example, by catalytic hydrogenation in an acidic medium and in the presence of palladium.

The halogenation is carried out with 4 or 5 equivalents of N-halosuccinimide (for example N-chlorosuccinimide), according to whether the intermediate of general formula (IV) for which $R_2$ is hydrogen or otherwise is used as starting material. The procedure is advantageously carried out in a chlorinated solvent (dichloromethane or dichloroethane for example) or in a nitrile (acetonitrile for example) at the reflux temperature of the reaction mixture.

The reduction of the ketone functional group to a hydroxyl can be carried out with an alkali metal borohydride, for example sodium cyanoborohydride, in an alcoholic medium at a temperature of between 20 and 40° C. The dehydration can be carried out with an acid such as in particular p-toluenesulphonic acid in an organic solvent such as toluene for example, at the reflux temperature of the reaction mixture.

The conversion of the ketone functional group to the imine can be obtained for example by application or adaptation of the methods described in Org. Synth., 5, 191; Org. Synth., 54, 46 or Synthesis 6(2), 629 1985). The reduction to an amine can be carried out by application or by analogy with the methods described in J. Org. Chem., 51, 3635 (1986) or J. Med. Chem., 7, 381 (1964).

The conversion of the ketone functional group to an alkyloxy can be carried out by treating with a trialkyl orthoformate, for example trimethyl orthoformate, in an alcoholic medium at the reflux temperature of the reaction mixture.

When it is desired to obtain a derivative as defined in b), the halogenation of the intermediate of general formula (IV) is carried out with an N-halosuccinimide, followed where appropriate by treatment with an alcoholate or a thiolate.

The halogenation is carried out with 2 or 3 equivalents of N-halosuccinimide, according to whether or not it is desired to obtain a product for which $R_2$ is a halogen atom (from the corresponding derivative for which $R_2$ is a hydrogen atom). The procedure is advantageously carried out in a chlorinated solvent (dichloromethane or dichloroethane for example) or in a nitrile (acetonitrile for example) at the reflux temperature of the reaction mixture.

The treatment with an alcoholate (for example sodium methoxide) or with a thiolate (for example sodium thiomethoxide) is carried out in toluene, at the reflux temperature of the reaction mixture.

The hydrolysis of the nitrile to an amide is carried out according to known methods, in particular by heating in an alkaline medium in an organic solvent, for example t-butanol at a temperature of between 30 and 85° C., or in a concentrated acidic medium at a temperature of between 20 and 100° C.

The hydrolysis of the ester or of the nitrile to an acid is carried out according to known methods, in particular in a basic medium in an alcohol with a high boiling point, for example in the presence of potassium hydroxide in ethylene glycol, at a temperature of between 100° C. and the reflux temperature of the reaction mixture.

The conversion of the acid functional group Hto an alkyloxycarbonyl radical is carried out by the usual esterification methods which do not alter the rest of the molecule, in particular by application or adaptation of the methods described in Tetrahedron, 33, 683 (1977), Tetrahedron Letters, 4475 (1978) or Bull. Soc. Chim. Japan, 40, 2380 (1967).

The conversion of the acid functional group to an imidazole-containing radical is carried out in a solvent such as tetrahydrofuran at a temperature of between 20 and 40° C.

The conversion to an acetyl radical is carried out using, as starting material, the derivative for which $R_1$ is carboxyl, by preparing the acid halide and then by the action of a malonic derivative (for example methyl malonate), followed by decarboxylation of the derivative obtained. The procedure is carried out under the conditions described or by analogy with the conditions described in Tetrahedron, 14, 321 (1961); Org. Synth., 3, 169; J. Org. Chem., 50, 2622 (1987); Synthesis, 284 (1982).

The oxidation of the pyridyl radical to pyridyl N-oxide is carried out by any oxidation method which does not alter the rest of the molecule. In particular, the procedure is carried out by means of a peracid such as m-chloroperbenzoic acid, in an alcoholic medium (ethanol for example) at a temperature of between 15 and 30° C.

When - - - is a single bond, the derivatives of general formula (I) exhibit stereoisomeric forms. These forms are separated by known methods, in particular by chromatography on a chiral phase. It is understood that the present invention also relates to the stereoisomers of the products of general formula (I) when these exist, as well as mixtures thereof.

The products according to the invention which carry an amino or alkylamino radical may be converted to acid addition salts by known methods. It is understood that these salts are also within the scope of the present invention.

As examples of addition salts with pharmaceutically acceptable acids, there may be mentioned the salts formed with inorganic acids (hydrochlorides, hydrobromides, sulphates, nitrates, phosphates) or with organic acids (succinates, fumarates, tartrates, acetates, propionates, maleates, citrates, methanesulphonates, p-toluenesulphonates, isethionates, or with substitution derivatives of these compounds).

The present invention also relates to the pyrrole derivatives of general formula (I) in which when - - - is a double bond, $R_2$ is a chlorine atom when simultaneously $R_4$ is hydrogen or halogen, $R_5$ is hydrogen, and when $R_1$ is cyano, carboxamido, alkyloxycarbonyl or acetyl, and Het-$R_3$ is 3-pyridyl optionally substituted with methyl, chlorine or fluorine at the 2 position [hereinafter called structure (I')], for their use as a medicament. These products have in particular proved very advantageous in the treatment and/or prophylaxis of conditions in which a virus of the herpes family is involved, and/or in which TNF is involved.

The action of the derivatives of general formula (I) on viruses of the herpes family has been demonstrated in the techniques described by NEYTS et al., Virology, 179, 41–50 (1990); Andrei et al., Eur. J. Clin. Microbiol. Infect. Dis., 10, 1026–1033 (1991); or in the technique described by Andrei et al., Eur. J. Clin. Microbiol. Infect. Dis., 11, 143–151 (1992), Reymen et al., Antiviral Res., 28, 343–357 (1995).

The technique used consists in the measurement of the cytopathogenic effect of the herpesvirus and of its protection by the use of products of general formula (I). The antiviral activity is assessed by measuring the $IC_{50}$ (concentration necessary to inhibit 50% of the cytopathogenic effect induced by the virus).

The activity of the products according to the invention on the human cytomegalovirus has been studied on the Davis and AD-169 strains. On the Davis strain, the products according to the invention proved active at $IC_{50}$ values of between 0.015 μg/ml and 20 μg/ml, and on the AD-169 strain, the products according to the invention proved active at $IC_{50}$ values of between 0.02 μg/ml and 20 μg/ml.

By way of example, the results obtained in these techniques for 4 products according to-the invention are given below:

TABLE I

| Example No. | AD-169 $IC_{50}$ (μg/ml) | Davis strain $IC_{50}$ (μg/ml) |
| --- | --- | --- |
| 1 | 1.15 | 0.5 |
|   | 0.32 | 0.5 |
| 2 | 0.5 | 0.43 |
|   | 0.86 | 0.72 |
| 7 [(R,S) form] | 0.2 | 0.027 |
|   | 0.02 | 0.015 |
| 8 | <0.2 | <0.2 |
|   | 0.05 | 0.02 |

Moreover, no product manifests cytotoxicity in vitro (50% inhibition of cell growth at the dose of 20 μg/ml)

The inhibitory activity of the compounds according to the invention towards the effects mediated by various cellular activators, including $TNF_\alpha$, has been demonstrated in the following manner:

The effects of the derivatives according to the invention on the reactivation of the HIV virus by $TNF_\alpha$ (10 Units/ml) or Phorbol Myristate Acetate (PMA at $10^{-7}$ M) were studied in U1 cells derived from the promonocytic line U937 [Folks et al., Science, 238, 800 (1987)].

Experimental Study:

The product to be studied is dissolved in dimethylformamide (DMF) or dimethyl sulphoxide (DMSO). The stock solutions are stored at a temperature of 4° C. and diluted in culture medium on the day of the experiment so that the solvent concentration is constant (0.1%).

The U1 cells are pretreated 5 hours before stimulation with product concentrations ranging from 0.001 μM to 10 μM. Three days after induction, the viral supernatant is collected and the reverse transcriptase activity reflecting viral production is evaluated (SPA test).

The reverse transcriptase activity is measured by known techniques, in duplicate [Strebel et al., Nature, 328, 728 (1987)].

Some controls do not receive the activator. Other controls do not receive the product to be studied. Others receive neither the product nor the activator.

Results:

The decrease in viral production caused by the derivatives according to the invention is significant and dose-dependent in the case of U1 cells treated with $TNF_\alpha$ or with PMA. On day 3, a decrease of at least 50% in the production of reverse transcriptase is observed for the U1 cells stimulated with 10 units/ml of $TNF_\alpha$ and treated with a concentration of 10 μM of product.

Moreover, no cytotoxicity of the test products is observed on cell viability at the concentration of 1 μM.

In this method, the compounds according to the invention have proved active at concentrations of between 0.01 μM and 10 μM.

Advantageous products are for example:

2-chloro-8-hydroxy-3-pyridin-3-yl-5,6,7,8-tetrahydroindolizine-1-carboxamide,
2-chloro-8-hydroxy-3-pyridin-3-yl-5,6,7,8-tetrahydroindolizine-1-carbonitrile, methyl 2-chloro-8-hydroxy-3-pyridin-3-yl-5,6,7,8-tetrahydroindolizine-1-carboxylate,
1-acetyl-2-chloro-8-hydroxy-3-pyridin-3-yl-5,6,7,8-tetrahydroindolizine,
2-chloro-8-hydroxy-3-(2-chloropyridin-3-yl)-5,6,7,8-tetrahydroindolizine-1-carboxamide,
2-chloro-8-hydroxy-3-(2-chloropyridin-3-yl)-5,6,7,8-tetrahydroindolizine-1-carbonitrile,
methyl 2-chloro-8-hydroxy-3-(2-chloropyridin-3-yl)-5,6,7,8-tetrahydroindolizine-1-carboxylate,
1-acetyl-2-chloro-8-hydroxy-3-(2-chloropyridin-3-yl)-5,6,7,8-tetrahydroindolizine,
2-chloro-8-hydroxy-3-(2-fluoropyridin-3-yl)-5,6,7,8-tetrahydroindolizine-1-carboxamide,
2-chloro-8-hydroxy-3-(2-fluoropyridin-3-yl)-5,6,7,8-tetrahydroindolizine-1-carbonitrile,
methyl 2-chloro-8-hydroxy-3-(2-fluoropyridin-3-yl)-5,6,7,8-tetrahydroindolizine-1-carboxylate,
1-acetyl-2-chloro-8-hydroxy-3-(2-fluoropyridin-3-yl)-5,6,7,8-tetrahydroindolizine,
2-chloro-8-methoxy-3-pyridin-3-yl-5,6,7,8-tetrahydroindolizine-1-carboxamide,
2-chloro-8-methoxy-3-pyridin-3-yl-5,6,7,8-tetrahydroindolizine-1-carbonitrile,
methyl 2-chloro-8-methoxy-3-pyridin-3-yl-5,6,7,8-tetrahydroindolizine-1-carboxylate,
1-acetyl-2-chloro-8-methoxy-3-pyridin-3-yl-5,6,7,8-tetrahydroindolizine,
2-chloro-8-methoxy-3-(2-chloropyridin-3-yl)-5,6,7,8-tetrahydroindolizine-1-carboxamide,
2-chloro-8-methoxy-3-(2-chloropyridin-3-yl)-5,6,7,8-tetrahydroindolizine-1-carbonitrile,
methyl 2-chloro-8-methoxy-3-(2-chloropyridin-3-yl)-5,6,7,8-tetrahydroindolizine-1-carboxylate,
1-acetyl-2-chloro-8-methoxy-3-(2-chloropyridin-3-yl)-5,6,7,8-tetrahydroindolizine,
2-chloro-8-methoxy-3-(2-fluoropyridin-3-yl)-5,6,7,8-tetrahydroindolizine-1-carboxamide,
2-chloro-8-methoxy-3-(2-fluoropyridin-3-yl)-5,6,7,8-tetrahydroindolizine-1-carbonitrile,
methyl 2-chloro-8-methoxy-3-(2-fluoropyridin-3-yl)-5,6,7,8-tetrahydroindolizine-1-carboxylate,
1-acetyl-2-chloro-8-methoxy-3-(2-fluoropyridin-3-yl)-5,6,7,8-tetrahydroindolizine,
2-cyano-8-hydroxy-3-pyridin-3-yl-5,6,7,8-tetrahydroindolizine-1-carboxamide,
2-cyano-8-hydroxy-3-pyridin-3-yl-5,6,7,8-tetrahydroindolizine-1-carbonitrile,
methyl 2-cyano-8-hydroxy-3-pyridin-3-yl-5,6,7,8-tetrahydroindolizine-1-carboxylate,
1-acetyl-2-cyano-8-hydroxy-3-pyridin-3-yl-5,6,7,8-tetrahydroindolizine,
2-cyano-8-hydroxy-3-(2-chloropyridin-3-yl)-5,6,7,8-tetrahydroindolizine-1-carboxamide,
2-cyano-8-hydroxy-3-(2-chloropyridin-3-yl)-5,6,7,8-tetrahydroindolizine-1-carbonitrile,
methyl 2-cyano-8-hydroxy-3-(2-chloropyridin-3-yl)-5,6,7,8-tetrahydroindolizine-1-carboxylate,
1-acetyl-2-cyano-8-hydroxy-3-(2-chloropyridin-3-yl)-5,6,7,8-tetrahydroindolizine,
2-cyano-8-hydroxy-3-(2-fluoropyridin-3-yl)-5,6,7,8-tetrahydroindolizine-1-carboxamide,
2-cyano-8-hydroxy-3-(2-fluoropyridin-3-yl)-5,6,7,8-tetrahydroindolizine-1-carbonitrile,
methyl 2-cyano-8-hydroxy-3-(2-fluoropyridin-3-yl)-5,6,7,8-tetrahydroindolizine-1-carboxylate,
1-acetyl-2-cyano-8-hydroxy-3-(2-fluoropyridin-3-yl)-5,6,7,8-tetrahydroindolizine,
2-methoxy-8-hydroxy-3-pyridin-3-yl-5,6,7,8-tetrahydroindolizine-1-carboxamide,
2-methoxy-8-hydroxy-3-pyridin-3-yl-5,6,7,8-tetrahydroindolizine-1-carbonitrile,
methyl 2-methoxy-8-hydroxy-3-pyridin-3-yl-5,6,7,8-tetrahydroindolizine-1-carboxylate,
1-acetyl-2-methoxy-8-hydroxy-3-pyridin-3-yl-5,6,7,8-tetrahydroindolizine,
2-methoxy-8-hydroxy-3-(2-chloropyridin-3-yl)-5,6,7,8-tetrahydroindolizine-1-carboxamide,
2-methoxy-8-hydroxy-3-(2-chloropyridin-3-yl)-5,6,7,8-tetrahydroindolizine-1-carbonitrile,
methyl 2-methoxy-8-hydroxy-3-(2-chloropyridin-3-yl)-5,6,7,8-tetrahydroindolizine-1-carboxylate,
1-acetyl-2-methoxy-8-hydroxy-3-(2-chloropyridin-3-yl)-5,6,7,8-tetrahydroindolizine,
2-methoxy-8-hydroxy-3-(2-fluoropyridin-3-yl)-5,6,7,8-tetrahydroindolizine-1-carboxamide,
2-methoxy-8-hydroxy-3-(2-fluoropyridin-3-yl)-5,6,7,8-tetrahydroindolizine-1-carbonitrile,
methyl 2-methoxy-8-hydroxy-3-(2-fluoropyridin-3-yl)-5,6,7,8-tetrahydroindolizine-1-carboxylate,
1-acetyl-2-methoxy-8-hydroxy-3-(2-fluoropyridin-3-yl)-5,6,7,8-tetrahydroindolizine,
2-methyl-8-hydroxy-3-pyridin-3-yl-5,6,7,8-tetrahydroindolizine-1-carboxamide,
2-methyl-8-hydroxy-3-pyridin-3-yl-5,6,7,8-tetrahydroindolizine-1-carbonitrile,
methyl 2-methyl-8-hydroxy-3-pyridin-3-yl-5,6,7,8-tetrahydroindolizine-1-carboxylate,
1-acetyl-2-methyl-8-hydroxy-3-pyridin-3-yl-5,6,7,8-tetrahydroindolizine,
2-methyl-8-hydroxy-3-(2-chloropyridin-3-yl)-5,6,7,8-tetrahydroindolizine-1-carboxamide,
2-methyl-8-hydroxy-3-(2-chloropyridin-3-yl)-5,6,7,8-tetrahydroindolizine-1-carbonitrile,
methyl 2-methyl-8-hydroxy-3-(2-chloropyridin-3-yl)-5,6,7,8-tetrahydroindolizine-1-carboxylate,
1-acetyl-2-methyl-8-hydroxy-3-(2-chloropyridin-3-yl)-5,6,7,8-tetrahydroindolizine,
2-methyl-8-hydroxy-3-(2-fluoropyridin-3-yl)-5,6,7,8-tetrahydroindolizine-1-carboxamide,
2-methyl-8-hydroxy-3-(2-fluoropyridin-3-yl)-5,6,7,8-tetrahydroindolizine-1-carbonitrile,
methyl 2-methyl-8-hydroxy-3-(2-fluoropyridin-3-yl)-5,6,7,8-tetrahydroindolizine-1-carboxylate,
1-acetyl-2-methyl-8-hydroxy-3-(2-fluoropyridin-3-yl)-5,6,7,8-tetrahydroindolizine,
2-trifluoromethyl-8-hydroxy-3-pyridin-3-yl-5,6,7,8-tetrahydroindolizine-1-carboxamide,
2-trifluoromethyl-8-hydroxy-3-pyridin-3-yl-5,6,7,8-tetrahydroindolizine-1-carbonitrile,
methyl 2-trifluoromethyl-8-hydroxy-3-pyridin-3-yl-5,6,7,8-tetrahydroindolizine-1-carboxylate,
1-acetyl-2-trifluoromethyl-8-hydroxy-3-pyridin-3-yl-5,6,7,8-tetrahydroindolizine,
2-trifluoromethyl-8-hydroxy-3-(2-chloropyridin-3-yl)-5,6,7,8-tetrahydroindolizine-1-carboxamide,
2-trifluoromethyl-8-hydroxy-3-(2-chloropyridin-3-yl)-5,6,7,8-tetrahydroindolizine-1-carbonitrile, methyl 2-trifluoromethyl-8-hydroxy-3-(2-chloropyridin-3-yl)-5,6,7,8-tetrahydroindolizine-1-carboxylate,
1-acetyl-2-trifluoromethyl-8-hydroxy-3-(2-chloropyridin-3-yl)-5,6,7,8-tetrahydroindolizine,
2-trifluoromethyl-8-hydroxy-3-(2-fluoropyridin-3-yl)-5,6,7,8-tetrahydroindolizine-1-carboxamide,
2-trifluoromethyl-8-hydroxy-3-(2-fluoropyridin-3-yl)-5,6,7,8-tetrahydroindolizine-1-carbonitrile,
methyl 2-trifluoromethyl-8-hydroxy-3-(2-fluoropyridin-3-yl)-5,6,7,8-tetrahydroindolizine-1-carboxylate,
1-acetyl-2-trifluoromethyl-8-hydroxy-3-(2-fluoropyridin-3-yl)-5,6,7,8-tetrahydroindolizine,
2-chloro-3-pyridin-3-yl-5,6-dihydroindolizine-1-carboxamide,
2-chloro-3-pyridin-3-yl-5,6-dihydroindolizine-1-carbonitrile,
methyl 2-chloro-3-pyridin-3-yl-5,6-dihydroindolizine-1-carboxylate,
1-acetyl-2-chloro-3-pyridin-3-yl-5,6-dihydroindolizine,
2-chloro-3-(2-chloropyridin-3-yl)-5,6-dihydroindolizine-1-carboxamide,
2-chloro-3-(2-chloropyridin-3-yl)-5,6-dihydroindolizine-1-carbonitrile,
methyl 2-chloro-3-(2-chloropyridin-3-yl)-5,6-dihydroindolizine-1-carboxylate,
1-acetyl-2-chloro-3-(2-chloropyridin-3-yl)-5,6-dihydroindolizine,
2-chloro-3-(2-fluoropyridin-3-yl)-5,6-dihydroindolizine-1-carboxamide,
2-chloro-3-(2-fluoropyridin-3-yl)-5,6-dihydroindolizine-1-carbonitrile,
methyl 2-chloro-3-(2-fluoropyridin-3-yl)-5,6-dihydroindolizine-1-carboxylate,
1-acetyl-2-chloro-3-(2-fluoropyridin-3-yl)-5,6-dihydroindolizine,
2-chloro-7-methoxy-3-pyridin-3-yl-5,6-dihydroindolizine-1-carboxamide,
2-chloro-7-methoxy-3-pyridin-3-yl-5,6-dihydroindolizine-1-carbonitrile,
methyl 2-chloro-7-methoxy-3-pyridin-3-yl-5,6-dihydroindolizine-1-carboxylate,
1-acetyl-2-chloro-7-methoxy-3-pyridin-3-yl-5,6-dihydroindolizine,
2-chloro-7-methoxy-3-(2-chloropyridin-3-yl)-5,6-dihydroindolizine-1-carboxamide,
2-chloro-7-methoxy-3-(2-chloropyridin-3-yl)-5,6-dihydroindolizine-1-carbonitrile,
methyl 2-chloro-7-methoxy-3-(2-chloropyridin-3-yl)-5,6-dihydroindolizine-1-carboxylate,
1-acetyl-2-chloro-7-methoxy-3-(2-chloropyridin-3-yl)-5,6-dihydroindolizine,
2-chloro-7-methoxy-3-(2-fluoropyridin-3-yl)-5,6-dihydroindolizine-1-carboxamide,
2-chloro-7-methoxy-3-(2-fluoropyridin-3-yl)-5,6-dihydroindolizine-1-carbonitrile,
methyl 2-chloro-7-methoxy-3-(2-fluoropyridin-3-yl)-5,6-dihydroindolizine-1-carboxylate,
1-acetyl-2-chloro-7-methoxy-3-(2-fluoropyridin-3-yl)-5,6-dihydroindolizine,
2,7-dichloro-3-pyridin-3-yl-5,6-dihydroindolizine-1-carboxamide,
2,7-dichloro-3-pyridin-3-yl-5,6-dihydroindolizine-1-carbonitrile,
methyl 2,7-dichloro-3-pyridin-3-yl-5,6-dihydroindolizine-1-carboxylate,
1-acetyl-2,7-dichloro-3-pyridin-3-yl-5,6-dihydroindolizine,
2,7-dichloro-3-(2-chloropyridin-3-yl)-5,6-dihydroindolizine-1-carboxamide,
2,7-dichloro-3-(2-chloropyridin-3-yl)-5,6-dihydroindolizine-1-carbonitrile,
methyl 2,7-dichloro-3-(2-chloropyridin-3-yl)-5,6-dihydroindolizine-1-carboxylate,
1-acetyl-2,7-dichloro-3-(2-chloropyridin-3-yl)-5,6-dihydroindolizine,
2,7-dichloro-3-(2-fluoropyridin-3-yl)-5,6-dihydroindolizine-1-carboxamide,
2,7-dichloro-3-(2-fluoropyridin-3-yl)-5,6-dihydroindolizine-1-carbonitrile,
methyl 2,7-dichloro-3-(2-fluoropyridin-3-yl)-5,6-dihydroindolizine-1-carboxylate,
1-acetyl-2,7-dichloro-3-(2-fluoropyridin-3-yl)-5,6-dihydroindolizine,
2-cyano-3-pyridin-3-yl-5,6-dihydroindolizine-1-carboxamide,
2-cyano-3-pyridin-3-yl-5,6-dihydroindolizine-1-carbonitrile,
methyl 2-cyano-3-pyridin-3-yl-5,6-dihydroindolizine-1-carboxylate,
1-acetyl-2-cyano-3-pyridin-3-yl-5,6-dihydroindolizine,
2-cyano-3-(2-chloropyridin-3-yl)-5,6-dihydroindolizine-1-carboxamide,
2-cyano-3-(2-chloropyridin-3-yl)-5,6-dihydroindolizine-1-carbonitrile,
methyl 2-cyano-3-(2-chloropyridin-3-yl)-5,6-dihydroindolizine-1-carboxylate,
1-acetyl-2-cyano-3-(2-chloropyridin-3-yl)-5,6-dihydroindolizine,
2-cyano-3-(2-fluoropyridin-3-yl)-5,6-dihydroindolizine-1-carboxamide,
2-cyano-3-(2-fluoropyridin-3-yl)-5,6-dihydroindolizine-1-carbonitrile,
methyl 2-cyano-3-(2-fluoropyridin-3-yl)-5,6-dihydroindolizine-1-carboxylate,
1-acetyl-2-cyano-3-(2-fluoropyridin-3-yl)-5,6-dihydroindolizine,
2-methoxy-3-pyridin-3-yl-5,6-dihydroindolizine-1-carboxamide,
2-methoxy-3-pyridin-3-yl-5,6-dihydroindolizine-1-carbonitrile,
methyl 2-methoxy-3-pyridin-3-yl-5,6-dihydroindolizine-1-carboxylate,
1-acetyl-2-methoxy-3-pyridin-3-yl-5,6-dihydroindolizine,
2-methoxy-3-(2-chloropyridin-3-yl)-5,6-dihydroindolizine-1-carboxamide,
2-methoxy-3-(2-chloropyridin-3-yl)-5,6-dihydroindolizine-1-carbonitrile,
methyl 2-methoxy-3-(2-chloropyridin-3-yl)-5,6-dihydroindolizine-1-carboxylate,
1-acetyl-2-methoxy-3-(2-chloropyridin-3-yl)-5,6-dihydroindolizine,
2-methoxy-3-(2-fluoropyridin-3-yl)-5,6-dihydroindolizine-1-carboxamide,
2-methoxy-3-(2-fluoropyridin-3-yl)-5,6-dihydroindolizine-1-carbonitrile,
methyl 2-methoxy-3-(2-fluoropyridin-3-yl)-5,6-dihydroindolizine-1-carboxylate,
1-acetyl-2-methoxy-3-(2-fluoropyridin-3-yl)-5,6-dihydroindolizine,
2-methyl-3-pyridin-3-yl-5,6-dihydroindolizine-1-carboxamide,
2-methyl-3-pyridin-3-yl-5,6-dihydroindolizine-1-carbonitrile,
methyl 2-methyl-3-pyridin-3-yl-5,6-dihydroindolizine-1-carboxylate,
1-acetyl-2-methyl-3-pyridin-3-yl-5,6-dihydroindolizine, 2-methyl-3-(2-chloropyridin-3-yl)-5,6-dihydroindolizine-1-carboxamide,
2-methyl-3-(2-chloropyridin-3-yl)-5,6-dihydroindolizine-1-carbonitrile,
methyl 2-methyl-3-(2-chloropyridin-3-yl)-5,6-dihydroindolizine-1-carboxylate,
1-acetyl-2-methyl-3-(2-chloropyridin-3-yl)-5,6-dihydroindolizine,
2-methyl-3-(2-fluoropyridin-3-yl)-5,6-dihydroindolizine-1-carboxamide,
2-methyl-3-(2-fluoropyridin-3-yl)-5,6-dihydroindolizine-1-carbonitrile,
methyl 2-methyl-3-(2-fluoropyridin-3-yl)-5,6-dihydroindolizine-1-carboxylate,
1-acetyl-2-methyl-3-(2-fluoropyridin-3-yl)-5,6-dihydroindolizine,
2-trifluoromethyl-3-pyridin-3-yl-5,6-dihydroindolizine-1-carboxamide,
2-trifluoromethyl-3-pyridin-3-yl-5,6-dihydroindolizine-1-carbonitrile,
methyl 2-trifluoromethyl-3-pyridin-3-yl-5,6-dihydroindolizine-1-carboxylate,
1-acetyl-2-trifluoromethyl-3-pyridin-3-yl-5,6-dihydroindolizine,
2-trifluoromethyl-3-(2-chloropyridin-3-yl)-5,6-dihydroindolizine-1-carboxamide,
2-trifluoromethyl-3-(2-chloropyridin-3-yl)-5,6-dihydroindolizine-1-carbonitrile,
methyl 2-trifluoromethyl-3-(2-chloropyridin-3-yl)-5,6-dihydroindolizine-1-carboxylate,
1-acetyl-2-trifluoromethyl-3-(2-chloropyridin-3-yl)-5,6-dihydroindolizine,
2-trifluoromethyl-3-(2-fluoropyridin-3--yl)-5,6-dihydroindolizine-1-carboxamide,
2-trifluoromethyl-3-(2-fluoropyridin-3-yl)-5,6-dihydroindolizine-1-carbonitrile,
methyl 2-trifluoromethyl-3-(2-fluoropyridin-3-yl)-5,6-dihydroindolizine-1-carboxylate,
1-acetyl-2-trifluoromethyl-3-(2-fluoropyridin-3-yl)-5,6-dihydroindolizine.

In particular, the products of formula:

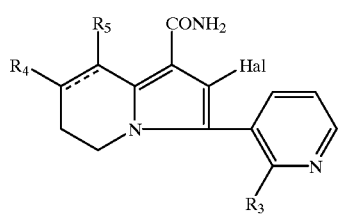

(VI)

for which:
Hal represents a halogen atom as defined above for $R_2$, and
a) the bond --- is a double bond,
$R_3$ is a hydrogen or halogen atom as defined above for $R_3$,
$R_4$ is a hydrogen or halogen atom as defined above for $R_4$, an alkyloxy or alkylthio radical optionally substituted with carboxyl or alkylamino in which the alkyl parts can form, with the nitrogen atom to which they are attached, a 4- to 6-membered heterocycle which may, in addition, comprise another heteroatom chosen from nitrogen, oxygen or sulphur, or phthalimido, and
$R_5$ is a hydrogen atom, or alternatively b) the bond --- is a single bond,
$R_3$ and $R_4$ are hydrogen atoms, and
$R_5$ is a hydroxyl or alkyloxy radical, the alkyl radicals being straight or branched and containing 1 to 4 carbon atoms, are more particularly advantageous.

Among these products, according to a preferred aspect of the invention,
Hal represents a chlorine atom, and
a) the bond --- is a double bond,
$R_3$ is a hydrogen or chlorine atom,
$R_4$ is hydrogen, chlorine, methoxy, methylthio, 2-(1,3-dioxo-1,3-dihydroisoindol-2-yl)ethylsulphanyl, or 2-aminoethylsulphanyl, and
$R_5$ is hydrogen, or alternatively
b) the bond --- is a single bond,
$R_3$ and $R_4$ are hydrogen, and
$R_5$ is hydroxyl or methoxy.

Still more preferably, the following compounds may be mentioned;
2-chloro-8-hydroxy-3-(pyridin-3-yl)-5,6,7,8-tetrahydroindolizine-1-carboxamide,
2-chloro-3-(pyridin-3-yl)-5,6-dihydroindolizine-1-carboxamide,
2-chloro-8-methoxy-3-(pyridin-3-yl)-5,6,7,8-tetrahydroindolizine-1-carboxamide,
2-chloro-7-methoxy-3-(pyridin-3-yl)-5,6-dihydroindolizine-1-carboxamide, and
2,7-dichloro-3-(pyridin-3-yl)-5,6-dihydroindolizine-1-carboxamide.

The pharmaceutical compositions containing pyrrole derivatives of general formula (I) and/or pyrrole derivatives of structure (I') are particularly advantageous because of the fact that they find application in many diseases of viral origin, particularly retinitis, pneumopathies, encephalitis, digestive infections and encephalitis caused by CMV, Kaposi's sarcoma, herpes labialis, genital herpes, herpetic encephalitis, varicella, roseola, zonas, hepatitis (caused by cytomegalovirus), ophthalmic infections or in the prophylaxis of the infection or of the viral reactivation. It may also be highly advantageous in the treatment and prevention of cardiovascular diseases, particularly in restenosis which may follow an angioplasty.

Likewise, the pharmaceutical compositions containing pyrrole derivatives of general formula (I) and/or pyrrole derivatives of structure (I') are also particularly advantageous because of the fact that they find applications in any of the pathologies involving cytokines including $TNF_\alpha$. By way of example, there may be mentioned: osteoarticular diseases of inflammatory origin, asthma, diabetes, cachexia (secondary to an infection or to a tumour), diseases of the digestive system such as Crohn's disease and ulcerohaemorrhagic rectocolitis, disorders of the central and/or peripheral nervous system, immunological diseases including graft-versus-host disease and allograft rejection, lesions due to perfusion and/or ischaemia, and viral or infectious diseases including pathologies related to HIV and to tuberculosis.

They are also advantageous for their applications in pathologies related to IL-8 reactivated by $TNF_\alpha$, such as psoriasis, inflammatory diseases of the digestive tube, respiratory distress syndrome, asthma, lesions induced by a perfusion, thrombosis, glomerulonephritis, and inflammatory osteoarticular pathologies.

They can also be used in pathologies involving adhesion molecules, for example diseases of the cardiovascular system (in particular artherosclerosis or thrombosis), lesions related to ischaemia-reperfusion, neurological disorders, digestive, pulmonary or articular inflammatory pathologies, immunological diseases including graft rejection.

The following examples, given with no limitation being implied, illustrate the invention:

EXAMPLE 1

A suspension of 2.4 g of 3-pyridin-3-yl-5,6,7,8-tetrahydroindolizine-1-carboxamide and 4.2 g of N-chlorosuccinimide in 600 cm$^3$ of acetonitrile is heated at the reflux temperature of acetonitrile for 3 hours. The reaction mixture is hydrolysed with 200 cm$^3$ of water is and then extracted with 3 times 300 cm$^3$ of ethyl acetate. The organic phases are dried over magnesium sulphate and then concentrated to dryness under reduced pressure (2.7 kPa) at a temprature close to 40° C. 2.51 g of a yellow powder are obtained, which powder is recrystallized from 65 cm$^3$ of acetonitrile. 1.25 g of 2,7-dichloro-3-pyridin-3-yl-5,6-dihydroindolizine-1-carboxamide are thus obtained in the form of a beige powder melting at 217° C.

EXAMPLE 2

A mixture of 6 g of 2,7-dichloro-3-pyridin-3-yl-5,6-dihydroindolizine-1-carboxamide and 5,24 g of sodium methoxide in 120 cm$^3$ of toluene and 0.4 cm$^3$ of methanol is heated at the reflux temperature of toluene for 5 days. The reaction mixture is hydrolysed with 100 cm$^3$ of water and then extracted with three times 100 cm$^3$ of dichloromethane. The organic phases are dried over magnesium sulphate and then concentrated to dryness under reduced pressure (2.7 kPa) at a temperature close to 40° C. 2.28 g of a yellow solid are obtained, which solid is chromatographed on a column 5.7 cm in diameter containing 580 g of silica (0.02–0.045). The elusion is carried out with a dichloromethane/ethyl acetate (80/20) mixture, at a pressure of 150 kPa, collecting 50 cm$^3$ fractions. The homogeneous fractions are pooled and concentrated to dryness under reduced pressure (2.7 kPa) at a temperature close to 40° C. 1.16 g of a yellow solid are obtained, which solid is recrystallized from 50 cm$^3$ of acetonitrile. 0.524 g of 2-chloro-7-methoxy-3-pyridin-3-yl-5,6-dihydroindolizine-1-carboxamide is obtained in the form of a white solid melting at 228° C.

3-Pyridin-3-yl-5,6,7,8-tetrahydroindolizine-1-carboxamide is prepared as described in European Patent Application EP 124 384.

EXAMPLE 3

A mixture of 0.616 g of 2,7-dichloro-3-pyridin-3-yl-5,6-dihydroindolizine-1-carboxamide and 0.28 g of sodium thiomethoxide in 30 cm$^3$ of dimethylformamide is heated at 57° C. for 5 hours. The reaction mixture is poured into 250 cm$^3$ of brine and then extracted with four times 80 cm$^3$ of dichloromethane. The organic phases are washed with three times 50 cm$^3$ of brine, dried over magnesium sulphate and then concentrated to dryness under reduced pressure (2.7 kPa) at a temperature close to 40° C. 0.6 g of an ochre-coloured crystallized product is obtained. This product is recrystallized from 75 cm$^3$ of acetonitrile. 0.29 g of 2-chloro-3-pyridin-3-yl-7-methylthio-5,6-dihydroindolizine-1-carboxamide is thus obtained in the form of a cream-coloured powder melting at 214° C.

2,7-Dichloro-3-pyridin-3-yl-5,6-dihydroindolizine-1-carboxamide is prepared as described in Example 1.

EXAMPLE 4

2.4 g of methyl 3-mercaptopropionate are dissolved in 100 cm$^3$ of dimethylformamide. 0.8 g of sodium hydride is added in small fractions, and then 3.08 g of 2,7-dichloro-3-pyridin-3-yl-5,6-dihydroindolizine-1-carboxamide in 80 cm$^3$ of dimethylformamide are poured in. The mixture is heated at 68° C. for 2 hours 30 minutes, and then poured into 25 cm$^3$ of hydrochloric acid (4 N). The mixture is concentrated to dryness under reduced pressure (1 kPa) at a temperature close to 60° C. The yellow residue obtained is taken up in 280 cm$^3$ of water and 10 cm$^3$ of hydrochloric acid (2 N), and then filtered and washed with twice 5 cm$^3$ of water. 1.1 g of 2-chloro-3-pyridin-3-yl-7-mercapto-5,6-dihydroindolizine-1-carboxamide are thus obtained in the form of a yellow powder melting at 232° C.

A mixture of 0.342 g of 2-chloro-3-pyridin-3-yl-7-mercapto-5,6-dihydroindolizine-1-carboxamide hydrochloride, 0.414 g of potassium carbonate and 0.381 g of N-(2-bromoethyl)phthalimide in 25 cm$^3$ of dimethylformamide is heated from 68° C. to 105° C. for 24 hours. The dimethylformamide is concentrated to dryness under reduced pressure (2.7 kPa) at a temperature close to 70° C. The oil obtained is taken up in 200 cm$^3$ of water and extracted with twice 100 cm$^3$ of dichloromethane. The organic phases are dried over magnesium sulphate and then concentrated to dryness under reduced pressure (2.7 kPa) at a temperature close to 50° C. 0.26 g of an orange-coloured residue is obtained which is chromatographed on a column 4 cm in diameter containing 6 g of silica (0.02–0.045). The elution is carried out with a dichloromethane/methanol (99/1) mixture, collecting 15 cm$^3$ fractions. The homogeneous fractions are pooled and concentrated to dryness under reduced pressure (2.7 kPa) at a temperature close to 40° C. 0.11 g of a yellow foam is thus obtained which is recrystallized from 12 cm$^3$ of acetonitrile. 0.050 g of 2-chloro-3-pyridin-3-yl-7-[2-(1,3-dioxo-1,3-dihydroisoindol-2-yl)ethylsulphanyl]-5,6-dihydroindolizine-1-carboxamide is thus obtained in the form of a yellow powder melting at 161° C.

2,7-Dichloro-3-pyridin-3-yl-5,6-dihydroindolizine-1-carboxamide is prepared as described in Example 1.

EXAMPLE 5

A mixture of 1.3 g of 2-chloro-3-pyridin-3-yl-7-[2-(1,3-dioxo-1,3-dihydroisoindol-2-yl)ethylsulphanyl]-5,6-dihydroindolizine-1-carboxamide and 1.16 cm$^3$ of hydrazine hydrate in 30 cm$^3$ of ethanol is heated at the reflux temperature of ethanol for 6 hours. The reaction mixture is concentrated to dryness under reduced pressure (2.7 kPa) at a temperature close to 40° C. The cream-coloured solid obtained is taken up in 80 cm$^3$ of water, and the pH is brought to 1 by addition of hydrochloric acid (4 N). The mixture is filtered and the solid is washed with twice 10 cm$^3$ of water. The clear yellow filtrate is brought to a pH of 10 by addition of sodium carbonate. The oil formed is extracted with three times 100 cm$^3$ of dichloromethane. The organic phases are dried over magnesium sulphate and then concentrated to dryness under reduced pressure (2.7 kPa) at a temperature close to 40° C. 0.6 g of an orange-coloured residue is obtained which is chromatographed on a column 3 cm in diameter containing 150 g of silica (0.02–0.045). The elution is carried out with a dichloromethane/methanol (50/50) mixture, collecting 20 cm$^3$ fractions. The homogeneous fractions are pooled and concentrated to dryness under reduced pressure (2.7 kPa) at a temperature close to 40° C. 0.4 g of a beige gummy crystallized product is obtained which is recrystallized from 25 cm$^3$ of ethanol and 5 cm$^3$ of hydrochloric ethanol (5 N). 0.29 g of 7-(2-aminoethylsulphanyl)-2-chloro-3-pyridin-3-yl-5,6-dihydroindolizine-1-carboxamide dihydrochloride is thus obtained in the form of a yellow powder melting at 175° C.

2-Chloro-3-pyridin-3-yl-7-[2-(1,3-dioxo-1,3-dihydroisoindol-2-yl)ethylsulphanyl-]-5,6-dihydroindolizine-1-carboxamide is prepared as described in Example 4.

EXAMPLE 6

2,7-Dichloro-3-(2-chloropyridin-3-yl)-5,6-dihydroindolizine-1-carboxamide is prepared as described in Example 1, but starting with 4.1 g of 3-(2-chloropyridin-3-yl)-5,6,7,8-tetrahydroindolizine-1-carboxamide and 6.3 g of N-chlorosuccinimide in 1000 cm³ of acetonitrile. 0.84 g of 2,7-dichloro-3-(2-chloropyridin-3-yl)-5,6-dihydroindolizine-1-carboxamide is obtained in the form of white floccules melting at 262° C.

3-(2-Chloropyridin-3-yl)-5,6,7,8-tetrahydroindolizine-1-carboxamide is described in Patent Application EP 124 384.

EXAMPLE 7

A mixture of 2.23 g of 3-pyridin-3-yl-5,6,7,8-tetrahydroindolizine-1-carbonitrile and 6.7 g of N-chlorosuccinimide in 200 cm³ of acetonitrile is heated at the reflux temperature of acetonitrile for 3 hours. The reaction mixture is hydrolysed with 300 cm³ of water and then extracted with three times 250 cm³ of dichloromethane. The organic phases are dried over magnesium sulphate and then concentrated to dryness under reduced pressure (2.7 kPa) at a temperature close to 40° C., and 2.84 g of residue are chromatographed on a column 4 cm in diameter containing 400 g of silica (0.04–0.063). The elution is carried out with ethyl acetate, at a pressure of 150 kPa, collecting 60 cm³ fractions. the homogeneous fractions are pooled and concentrated to dryness under reduced pressure (2.7 kPa) at a temperature close to 40° C. 1.67 g of a solid are thus obtained, which solid is recrystallized from 7.5 cm³ of acetonitrile. 650 mg of 2,7,7-trichloro-8-oxo-3-pyridin-3-yl-5,6,7,8-tetrahydro-indolizine-1-carbonitrile are obtained in the form of an orange-coloured powder melting at 220° C.

A suspension of 10.14 g of 2,7,7-trichloro-8-oxo-3-pyridin-3-yl-5,6,7,8-tetrahydroindolizine-1-carbonitrile and 300 cm³ of acetic acid in 1000 cm³ of ethanol is stirred under argon, and 3.06 g of 10% palladium on carbon in 50 cm³ of ethanol are added. The reaction mixture is bubbled with hydrogen for 2 hours at room temperature, and then filtered on No. 3 sintered glass covered with Celite. The cake is washed with twice 50 cm³ of ethanol and the filtrate is then concentrated to dryness under reduced pressure (2.7 kPa) at a temperature close to 55° C. An oily residue is taken up in 150 cm³ of water and the pH is brought to 8–9 by addition of sodium hydrogen carbonate. 7.08 g of 2-chloro-8-oxo-3-pyridin-3-yl-5,6,7,8-tetrahydroindolizine-1-carbonitrile are obtained in the form of a white solid melting at a temperature greater than 260° C.

10.33 g of 2-chloro-8-oxo-3-pyridin-3-yl-5,6,7,8-tetrahydroindolizine-1-carbonitrile in 70 cm³ of 60% sulphuric acid are heated at 85° C. for 8 hours. The mixture is hydrolysed with 100 cm³ of water and the pH is brought to 8–9 by addition of sodium hydrogen carbonate. A brown precipitate is filtered off and dissolved in 300 cm³ of dichloromethane. The organic phase is washed with 200 cm³ of water and dried over magnesium sulphate, and then concentrated to dryness under reduced pressure (2.7 kPa) at a temperature close to 40° C. 12 g of a wet brown solid are obtained, which solid is chromatographed on a column 7.7 cm in diameter containing 1.9 kg of silica (0.02–0.045). The elution is carried out with a dichloromethane/methanol (95/5) mixture, at a pressure of 150 kPa, collecting 60 cm³ fractions. The homogeneous fractions are pooled and concentrated to dryness under reduced pressure (2.7 kPa) at a temperature close to 40° C. 5.4 g of 2-chloro-8-oxo-3-pyridin-3-yl-5,6,7,8-tetrahydroindolizine-1-carboxamide are obtained in the form of a white solid melting at 234° C.

A mixture of 3 g of 2-chloro-8-oxo-3-pyridin-3-yl-5,6,7,8-tetrahydroindolizine-1-carboxamide in 1000 cm³ of methanol is stirred under argon until complete dissolution. 10 mg of bromocresol green are added, and 0.946 g of sodium cyanoborohydride in 10 cm³ of methanol is added dropwise. When the reaction mixture becomes blue-green, a saturated solution of hydrochloric ethanol is added dropwise until the yellow colour disappears. The mixture is kept stirring at room temperature for 48 hours, and then concentrated to dryness under reduced pressure (2.7 kPa) at a temperature close to 40° C. The residue is taken up in 150 cm³ of water and the pH is brought to 8–9 by addition of sodium hydrogen carbonate. The aqueous phase is extracted with three times 150 am³ of dichloromethane. The organic phases are dried over is magnesium sulphate and concentrated to dryness under reduced pressure (2.7 kPa) at a temperature close to 40° C. 2.5 g of a white solid are obtained, which solid is recrystallized from 55 cm³ of acetonitrile. 1.99 g of (R,S)-2-chloro-8-hydroxy-3-pyridin-3-yl-5,6,7,8-tetrahydroindolizine-1-carboxamide are obtained in the form of a white powder melting at 201° C.

The enantiomers of (R,S)-2-chloro-8-hydroxy-3-pyridin-3-yl-5,6,7,8-tetrahydroindolizine-1-carboxamide can be separated in the following manner:

2 g of (R,S)-2-chloro-8-hydroxy-3-pyridin-3-yl-5,6,7,8-tetrahydroindolizine-1-carboxamide are separated by high-performance liquid chromatography on a CHIRALPAK AD stationary chiral phase (4.6×250 mm). The mobile phase is a 50/50 mixture of heptane and ethanol, the flow rate is 1 ml/min. 1.164 g of the dextrorotatory enantiomer $[\alpha]_D^{20}$=+14.8±0.6 (c=0.5; dimethylformamide) and 1.053 g of the laevorotatory enantiomer $[\alpha]_D^{20}$=−15.8±0.6 (c=0.5; dimethylformamide) are obtained.

3-pyridin-3-yl-5,6,7,8-tetrahydroindolizine-1-carbonitrile is prepared as described in European Patent Application EP 124 384.

EXAMPLE 8

A suspension of 1.36 g of (R,S)-2-chloro-8-hydroxy-3-pyridin-3-yl-5,6,7,8-tetrahydroindolizine-1-carboxamide and 0.975 g of p-toluenesulphonic acid monohydrate in 160 cm³ of toluene is heated at the reflux temperature of toluene for 16 hours.

The reaction mixture is concentrated to dryness under reduced pressure (2.7 kPa) at a temperature close to 55° C. 0.9 g of a yellow solid is obtained which is recrystallized from 10 cm³ of isopropanol. 0.469 g of 2-chloro-3-pyridin-3-yl-5,6-dihydroindolizine-1-carboxamide is obtained in the form of a yellow solid melting at 195° C.

EXAMPLE 9

A mixture of 20 g of 3-pyridin-3-yl-5,6,7,8-tetrahydroindolizine-1-carbonitrile and 56.8 g of N-chlorosuccinimide in 1600 cm³ of acetonitrile is heated at the reflux temperature of acetonitrile for 3 hours. 150 cm³ of hydrochloric acid (1 N) and 150 cm³ of water are added to the reaction mixture. The reaction mixture is concentrated to dryness under reduced pressure (2.7 kPa) at a temperature close to 55° C. The residue obtained is taken up in 200 cm³ of water, and the pH is brought to 8–9 by addition of sodium hydrogen carbonate as a powder. After filtration, 29.23 g of a light brown solid are obtained, which solid is chromatographed on a column 10 cm in diameter containing 2000 g of silica (0.02–0.045). The elution is carried out with dichloromethane, collecting 70 cm$^3$ fractions. The homogeneous fractions are pooled and concentrated to dryness under reduced pressure (2.7 kPa) at a temperature close to 40° C. 20.75 g of 2,7,7-trichloro-8-oxo-3-pyridin-3-yl-5,6,7-trihydroindolizine-1-carbonitrile are thus obtained in the form of a powder melting at 228° C.

6.48 g of palladium on carbon (10%) in suspension in ethanol are added to a mixture of 20.75 g of 2,7,7-trichloro-8-oxo-3-pyridin-3-yl-5,6,7-trihydroindolizine-1-carbonitrile, 2000 cm$^3$ of ethanol, 600 cm$^3$ of acetic acid and 5.2 cm$^3$ of hydrochloric acid (12 N). A stream of hydrogen is passed through for 3 hours. The reaction mixture is filtered on Celite and then washed with twice 100 cm$^3$ of ethanol. The filtrate is concentrated to dryness under reduced pressure (2.7 kPa) at a temperature close to 60° C. The orange-coloured solid obtained is taken up in 200 cm$^3$ of water, and the pH is brought to 8–9 by addition of sodium hydrogen carbonate, and then filtered and washed with twice 20 cm$^3$ of water. 0.5 g of 2-chloro-3-pyridin-3-yl-5,6,7-trihydro-8-oxoindolizine-1-carbonitrile is thus obtained in the form of a yellow solid melting at a temperature greater than 260° C.

A mixture of 2.717 g of 2-chloro-3-pyridin-3-yl-5,6,7-trihydro-8-oxoindolizine-1-carbonitrile, 1 cm$^3$ of hydrochloric methanol (3.8 N), and 5.5 cm$^3$ of trimethyl orthoformate in 200 cm$^3$ of methanol is heated at the reflux temperature of methanol for 12 hours. The reaction mixture is concentrated to dryness under reduced pressure (2.7 kPa) at a temperature close to 40° C. The beige solid obtained is taken up in 50 cm$^3$ of water and the pH is brought to 8–9 by addition of sodium hydrogen carbonate. After filtration, 2.6 g of a beige powder are obtained, which powder is chromatographed on a column 4 cm in diameter containing 35 g of silica (0.02–0.045). The elution is carried out with dichloromethane and then with a dichloromethane/ethyl acetate (80/20) mixture, collecting 50 cm$^3$ fractions. The homogeneous fractions are pooled and concentrated to dryness under reduced pressure (2.7 kPa) at a temperature close to 40° C. 1.7 g of 2-chloro-8-methoxy-3-pyridin-3-yl-5,6-dihydroindolizine-1-carbonitrile are thus obtained in the form of a white powder melting at 229° C.

0.12 g of palladium on carbon (10%) is added to a mixture of 0.55 g of 2-chloro-8-methoxy-3-pyridin- 3-yl-5,6-dihydroindolizine-1-carbonitrile in 5 cm$^3$ of methanol. A stream of hydrogen is passed through for 14 hours. The reaction mixture is filtered on Celite and then washed with twice 40 cm$^3$ of methanol. The filtrate is concentrated to dryness under reduced pressure (2.7 kPa) at a temperature close to 50° C. 0.49 g of a beige semicrystallized product is obtained, which product is chromatographed on a column 2 cm in diameter containing 150 g of silica (0.02–0.045). The elution is carried out with a dichloromethane/methanol (95/5) mixture, collecting 15 cm$^3$ fractions. The homogeneous fractions are pooled and concentrated to dryness under reduced pressure (2.7 kPa) at a temperature close to 40° C. 0.12 g of 2-chloro-8-methoxy-3-pyridin-3-yl-5,6,7,8-tetrahydroindolizine-1-carbonitrile is thus obtained in the form of a yellow oil.

Rf=0.49 dichloromethane/methanol (95/5).

A mixture of 0.23 g of 2-chloro-8-methoxy-3-pyridin-3-yl-5,6,7,8-tetrahydroindolizine-1-carbonitrile and 0.16 g of potassium hydroxide in 15 cm$^3$ of tert-butanol is heated at the reflux temperature of tert-butanol for 12 hours. The reaction mixture is concentrated to dryness under reduced pressure (2.7 kPa) at a temperature close to 50° C. The oil obtained is taken up in 7 cm$^3$ of water and extracted with four times 30 cm$^3$ of dichloromethane. The organic phases are dried over magnesium sulphate and then concentrated to dryness under reduced pressure (2.7 kPa) at a temperature close to 40° C. 0.125 g of a vitreous residue is obtained which is chromatographed on a column 2 cm in diameter containing 100 g of silica (0.02–0.045). The elution is carried out with a dichloromethane/methanol (95/5) mixture, collecting 40 cm$^3$ fractions. The homogeneous fractions are pooled and concentrated to dryness under reduced pressure (2.7 kPa) at a temperature close to 40° C. 0.09 g of a semisolid is obtained which is recrystallized from 1.1 cm$^3$ of acetonitrile. 0.0277 g of 2-chloro-8-methoxy-3-pyridin-3-yl-5,6,7,8-tetrahydro-indolizine-1-carboxamide is thus obtained in the form of a white powder melting at 166° C.

3-Pyridin-3-yl-5,6,7,8-tetrahydroindolizine-1-carbonitrile is described in Patent EP 124 384.

EXAMPLE 10

8-Oxo-2-chloro-3-pyridin-3-yl-5,6,7,8-tetrahydroindolizine-1-carbonitrile is prepared as described in Example 3.

A mixture containing 2 g of 8-oxo-2-chloro-3-pyridin-3-yl-5,6,7,8-tetrahydroindolizine-1-carbonitrile and 4.81 cm$^3$ of benzylamine is heated at a temperature of 150° C. for 20 minutes. The mixture is then hydrolysed with 50 cm$^3$ of water and extracted with three times 50 cm$^3$ of dichloromethane. The organic phases are washed with twice 50 cm$^3$ of water and then dried over magnesium sulphate and then filtered and concentrated to dryness under reduced pressure (2.7 kPa) at a temperature close to 40° C. 5.17 g of a brown oil are obtained, which oil is chromatographed on a column 4.2 cm in diameter containing 430 g of silica (0.02–0.045). The elution is carried out with dichloromethane/methanol (95/5), collecting 30 cm$^3$ fractions. The homogeneous fractions are pooled and concentrated to dryness under reduced pressure (2.7 kPa) at a temperature close to 40° C. 1.14 g of 8-amino-2-chloro-3-pyridin-3-yl-5,6,7,8-tetrahydroindolizine-1-carbonitrile are obtained in the form of a yellow oil.

Rf=0.51 dichloromethane/methanol (95/5).

1.56 cm$^3$ of triethylamine and 0.625 g of chloroacetyl chloride are added to a mixture containing 1 g of 8-amino-2-chloro-3-pyridin-3-yl-5,6,7,8-tetrahydroindolizine-1-carbonitrile in 50 cm$^3$ of dichloromethane. The reaction mixture is kept stirring at room temperature for 24 hours and is then washed with three times 100 cm$^3$ of water. The organic phase is dried over magnesium sulphate and then filtered and concentrated to dryness under reduced pressure (2.7 kPa) at a temperature close to 40° C. 0.92 g of a black residue is obtained which is chromatographed on a column 2.5 cm in diameter containing 150 g of silica (0.02–0.045). The elution is carried out with a dichloromethane/methanol (95/5) mixture, collecting 10 cm$^3$ fractions. The homogeneous fractions are pooled and concentrated to dryness under reduced pressure (2.7 kPa) at a temperature close to 40° C. 0.78 g of a brown solid is obtained which is then recrystallized with 35 cm$^3$ of acetonitrile. 0.385 g of 2-chioro-N-(2-chloro-1-cyano-3-pyridin-3-yl-5,6,7,8-tetrahydroindolizin-8-yl)acetamide is thus obtained in the form of a pale yellow powder melting at 238° C.

The present invention also relates to the pharmaceutical compositions for the treatment and/or prophylaxis of conditions in which one or more viruses of the herpes family are involved and/or in which the cytokines, including TNF$_\alpha$, are involved, containing a pyrrole derivative of general formula (I) or a pyrrole derivative of structure (I'), optionally in the form of is a salt, in the pure state or in the form of a combination with one or more compatible and pharmaceutically acceptable diluents or adjuvants.

The pharmaceutical compositions according to the invention are capable of slowing the progression to the disease or of reducing its severity in the infected subjects.

They are capable of preventing or slowing, in immunosuppressed subjects, the progression of subjects infected with a virus of the herpes family to a worsened state of the disease.

The pharmaceutical compositions according to the invention are also capable of inhibiting the replication of retroviruses and therefore of slowing the progression to the disease and of reducing its severity in the infected subjects. In particular, in the case of HIV infections, by inhibiting the replication of this virus, they are capable of slowing the progression to AIDS or of reducing its severity in the infected subjects. The pharmaceutical compositions according to the invention can be used for preventive or curative purposes. "Preventive" is understood to mean the preventing of progression in subjects exhibiting immunodeficiency and/or infected with retroviruses.

Of course, in the case of treatment in immunosuppressed individuals, the constitution of these compositions will be adapted to the specific case of the digestive tract of these subjects.

The compositions can be used by the oral, parenteral, topical or rectal route.

Sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization can be achieved in several ways, for example by aseptisizing filtration, by incorporating sterilizing agents into the composition, by irradiation or by heating. They can also be prepared in the form of solid sterile compositions which can be dissolved at the time of use in a sterile injectable medium.

As solid compositions for oral administration, there may be used tablets, pills, powders or granules. In these compositions, the active product according to the invention (optionally combined with another pharmaceutically compatible product) is mixed with one or more inert diluents or adjuvants, such as sucrose, lactose or starch. These compositions may also comprise substances other than diluents, for example a lubricant such as magnesium stearate.

As liquid compositions for oral administration, there may be used emulsions which are pharmaceutically acceptable, solutions, suspensions, syrups, elixirs containing inert diluents such as water or paraffin oil. These compositions may also comprise substances other than the diluents, for example wetting, sweetening or flavouring products.

The compositions for topical administration may be for example creams, ointments or lotions.

The compositions for rectal administration are suppositories or rectal capsules, which contain, in addition to the active ingredient, excipients such as cocoa butter, semisynthetic glycerides or polyethylene glycols.

In general, the doctor will determine the dosage judged most appropriate according to the age, weight and factors specific to the product and to the subject to be treated. Generally, in adults, the doses are between 25 and 2000 mg per day.

It has, furthermore, been shown that the pyrrole derivatives of general formula (I) and the pyrrole derivatives of structure (I') act in synergy when they are combined with other antiviral agents active on viruses of the herpes family or when they are combined with other antiretrovirus agents. The present invention also relates to the combinations consisting of a pyrrole derivative of general formula (I) or of a pyrrole derivative of structure (I'), and of an active ingredient known for its activity on viruses of the herpes family or else known for its anti-retrovirus activity, optionally in the presence of pharmaceutically acceptable excipients.

The agents known for their activity on viruses of the herpes family which may be combined are chosen from agents which are compatible and chemically inert towards the pyrrole derivative according to the invention. In a non-limiting manner, these agents are chosen, for example, from cidofovir, ganciclovir, foscarnet, GS930 and 1263W94 and the like.

The antiretrovirus agents which can be combined are chosen from agents which are compatible and chemically inert towards the derivatives according to the invention. Without implying any limitation, these agents are chosen from inhibitors of reverse transcriptase [zidovudine (AZT), didanosine (DDI), dideoxycytidine (DDC), lamivudine (3TC), TIBO, neviparine, PMEA and the like], among the protease inhibitors [for example saquinovir, ABT-538, MK-639 and the like], or from tat and rev protein inhibitors.

The pharmaceutical compositions comprising such combinations are also within the scope of the present invention.

The following example given with no limitation being implied illustrates a composition according to the invention.

EXAMPLE

| | |
|---|---|
| (R,S)-2-chloro-8-hydroxy-3-(pyridin-3-yl)-5,6,7,8-tetrahydroindolizine-1-carboxamide | 25 mg |
| Magnesium stearate: 1% | 2 mg |
| ACDISOL: 1% | 2 mg |
| Colloidal silica: 0.5% | 1 mg |
| Lactose | 170 mg |

What is claimed is:

1. A pyrrole compound having the following formula (I), its stereoisomer, salt, or a mixture thereof:

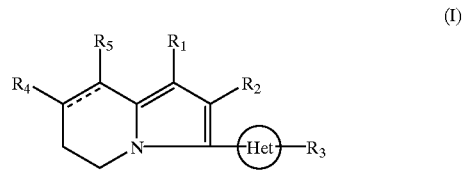

in which

R$_1$ is chosen from carboxamide, cyano, carboxyl, alkyloxycarbonyl, acetyl and imidazolylcarbonyl radicals, R$_3$ is chosen from a hydrogen atom, halogen atoms, alkyl radicals and hydroxyl radicals, and Het is chosen from pyridyl, pyridyl N-oxide and thiazolyl radicals, and
a) the bond --- is a single bond,
   $R_2$ is chosen from a hydrogen atom, halogen atoms, and cyano, alkyl, alkyloxy and trihalomethyl radicals,
   $R_4$ is a hydrogen atom, and
   $R_5$ is chosen from hydroxyl, alkyloxy, amino and haloacylamino radicals,
or alternatively
b) the bond --- a is a double bond, and
   $R_2$ is chosen from a hydrogen atom, halogen atoms, and cyano, alkyl, alkyloxy, alkenyl and trihalomethyl radicals,
   $R_4$ is chosen from a hydrogen atom, halogen atoms, alkyloxy radicals and alkylthio radicals which are unsubstituted or substituted with carboxyl, alkyloxycarbonyl, amino, alkylamino or dialkylamino in which the alkyl parts optionally form, with the nitrogen atom to which they are attached, phthalimido or a 4- to 6-membered heterocycle which optionally has another heteroatom chosen from nitrogen, oxygen and sulphur, and 2(1,3-dioxo-1,3-dihydroisoindol-2-yl)ethylsulphanyl, and
   $R_5$ is a hydrogen atom,
      wherein $R_2$ is not chlorine when simultaneously $R_4$ and $R_5$ are hydrogen, and when $R_1$ is cyano or carboxamido, and Het-$R_3$ is 3-pyridyl optionally substituted with fluorine at the 2 position, or alternatively simultaneously when $R_4$ is halogen, $R_5$ is hydrogen, and when $R_1$ is cyano or carboxamido and Het-$R_3$ is 3-pyridyl substituted with methyl, chlorine or fluorine at the 2 position or when $R_1$ is alkyloxycarbonyl or acetyl and when Het-$R_3$ is 3-pyridyl,
and wherein said alkyl radicals are straight or branched and contain from 1 to 4 carbon atoms and said acyl and alkenyl radicals are straight or branched and contain from 2 to 4 carbon atoms.

2. A pyrrole compound according to claim 1, wherein said pyrrole compound is chosen from:
   2-chloro-8-hydroxy-3-pyridin-3-yl-5,6,7,8-tetrahydroindolizine-1-carboxamide,
   2-chloro-8-hydroxy-3-pyridin-3-yl-5,6,7,8-tetrahydroindolizine-1-carbonitrile,
   methyl 2-chloro-8-hydroxy-3-pyridin-3-yl-5,6,7,8-tetrahydroindolizine-1-carboxylate,
   1-acetyl-2-chloro-8-hydroxy-3-pyridin-3-yl-5,6,7,8-tetrahydroindolizine,
   2-chloro-8-hydroxy-3-(2-chloropyridin-3-yl)-5,6,7,8-tetrahydroindolizine-1-carbonitrile,
   methyl 2-chloro-8-hydroxy-3-(2-chloropyridin-3-yl)5,6,7,8-tetrahydroindolizine-1-carboxylate,
   1-acetyl-2-chloro-8-hydroxy-3-(2-chloropyridin-3-yl)-5,6,7,8-tetrahydroindolizine,
   2-chloro-8-hydroxy-3-(2-fluoropyridin-3-yl)-5,6,7,8-tetrahydroindolizine-1-carboxamide,
   2-chloro-8-hydroxy-3-(2-fluoropyridin-3-yl)-5,6,7,8-tetrahydroindolizine-1-carbonitrile,
   methyl 2-chloro-8-hydroxy-3-(2-fluoropyridin-3-yl)5,6,7,8-tetrahydroindolizine-1-carboxylate,
   1-acetyl-2-chloro-8-hydroxy-3-(2-fluoropyridin-3-yl)-5,6,7,8-tetrahydroindolizine,
   2-chloro-8-methoxy-3-pyridin-3-yl-5,6,7,8-tetrahydroindolizine-1-carboxamide,
   2-chloro-8-methoxy-3-pyridin-3-yl-5,6,7,8-tetrahydroindolizine-1-carbonitrile,
   methyl 2-chloro-8-methoxy-3-pyridin-3-yl-5,6,7,8-tetrahydroindolizine-1-carboxylate,
   1-acetyl-2chloro-8-methoxy-3-pyridin-3-yl-5,6,7,8-tetrahydroindolizine,
   2-chloro-8-methoxy-3-(2-chloropyridin-3-yl)-5,6,7,8-tetrahydroindolizine-1-carboxamide,
   2-chloro-8-methoxy-3-(2-chloropyridin-3-yl)-5,6,7,8-tretrahydroindolizine-1-carbonitrile,
   methyl 2-chloro-8-methoxy-3-(2-chloropyridin-3-yl)-5,6,7,8-tetrahydroindolizine-1-carboxylate,
   1-acetyl-2-chloro-8-methoxy-3-(2-chloropyridin-3-yl)-5,6,7,8-tetrahydroindolizine,
   2-chloro-8-methoxy-3-(2-fluoropyridin-3-yl)-5,6,7,8-tetrahydroindolizine-1-carboxamide,
   2-chloro-8-methoxy-3-(2-fluoropyridin-3-yl)-5,6,7,8-tetrahydroindolizine-1-carbonitrile,
   methyl 2-chloro-8-methoxy-3-(2-fluoropyridin-3-yl)-5,6,7,8-tetrahydroindolizine-1-carboxylate,
   1-acetyl-2-chloro-8-methoxy-3-(2-fluoropyridin-3-yl)-5,6,7,8-tetrahydroindolizine,
   2-cyano-8-hydroxy-3-pyridin-3-yl-5,6,7,8-tetrahydroindolizine-1-carboxamide,
   2-cyano-8-hydroxy-3-pyridin-3-yl-5,6,7,8-tetrahydroindolizine-1-carbonitrile,
   methyl 2-cyano-8-hydroxy-3-pyridin-3-yl-5,6,7,8-tetrahydroindolizine-1-carboxylate,
   1-acetyl-2-cyano-8-hydroxy-3-pyridin-3-yl-5,6,7,8-tetrahydroindolizine,
   2-cyano-8-hydroxy-3-(2-chloropyridin-3-yl)-5,6,7,8-tetrahydroindolizine-1-carboxamide,
   2-cyano-8-hydroxy-3-(2-chloropyridin-3-yl)-5,6,7,8-tetrahydroindolizine-1-carbonitrile,
   methyl 2-cyano-8-hydroxy-3-(2-chloropyridin-3-yl)-5,6,7,8-tetrahydroindolizine-1-carboxylate,
   1-acetyl-2-cyano-8-hydroxy-3-(2-chloropyridin-3-yl)-5,6,7,8-tetrahydroindolizine,
   2-cyano-8-hydroxy-3-(2-fluoropyridin-3-yl)-5,6,7,8-tetrahydroindolizine-1-carboxamide,
   2-cyano-8-hydroxy-3-(2-fluoropyridin-3-yl)-5,6,7,8-tetrahydroindolizine-1-carbonitrile,
   methyl 2-cyano-8-hydroxy-3-(2-fluoropyridin-3-yl)-5,6,7,8-tetrahydroindolizine-1-carboxylate,
   1-acetyl-2-cyano-8-hydroxy-3-(2-fluoropyridin-3-yl)-5,6,7,8-tetrahydroindolizine,
   2-methoxy-8-hydroxy-3-pyridin-3-yl-5,6,7,8-tetrahydroindolizine-1-carboxamide,
   2-methoxy-8-hydroxy-3-pyridin-3-yl-5,6,7,8-tetrahydroindolizine-1-carbonitrile,
   methyl 2-methoxy-8-hydroxy-3-pyridin-3-yl-5,6,7,8-tetrahydroindolizine-1-carboxylate,
   1-acetyl-2-methoxy-8-hydroxy-3-pyridin-3-yl-5,6,7,8-tetrahydroindolizine,
   2-methoxy-8-hydroxy-3-(2-chloropyridin-3-yl)-5,6,7,8-tetrahydroindolizine-1-carboxamide,
   2-methoxy-8-hydroxy-3-(2-chloropyridin-3-yl)-5,6,7,8-tetrahydroindolizine-1-carbonitrile,
   methyl 2-methoxy-8-hydroxy-3-(2-chloropyridin-3-yl)-5,6,7,8-tetrahydroindolizine-1-carboxylate,
   1-acetyl-2-methoxy-8-hydroxy-3-(2-chloropyridin-3-yl)-5,6,7,8-tetrahydroindolizine,
   2-methoxy-8-hydroxy-3-(2-fluoropyridin-3-yl)-5,6,7,8-tetrahydroindolizine-1-carboxamide, 2-methoxy-8-hydroxy-3-(2-fluoropyridin-3-yl)-5,6,7,8-tetrahydroindolizine-1-carbonitrile, methyl 2-methoxy-8-hydroxy-3-(2-fluoropyridin-3-yl)-5,6,7,8-tetrahydroindolizine-1-carboxylate, 1-acetyl-2-methoxy-8-hydroxy-3-(2-fluoropyridin-3-yl)-5,6,7,8-tetrahydroindolizine, 2-methyl-8-hydroxy-3-pyridin-3-yl-5,6,7,8-tetrahydroindolizine-1-carboxamide, 2-methyl-8-hydroxy-3-pyridin-3-yl-5,6,7,8-tetrahydroindolizine-1-carbonitrile, methyl 2-methyl-8-hydroxy-3-pyridin-3-yl-5,6,7,8-tetrahydroindolizine-1-carboxylate, 1-acetyl-2-methyl-8-hydroxy-3-pyridin-3-yl-5,6,7,8-tetrahydroindolizine, 2-methyl-8-hydroxy-3-(2-chloropyridin-3-yl-5,6,7,8-tetrahydroindolizine-1-carboxamide, 2-methyl-8-hydroxy-3-(2-chloropyridin-3-yl)-5,6,7,8-tetrahydroindolizine-1-carbonitrile, methyl 2-methyl-8-hydroxy-3-(2-chloropyridin-3-yl)-5,6,7,8-tetrahydroindolizine-1-carboxylate, 1-acetyl-2-methyl-8-hydroxy-3-(2-chloropyridin-3-yl)-5,6,7,8-tetrahydroindolizine, 2-methyl-8-hydroxy-3-(2-fluoropyridin-3-yl)5,6,7,8-tetrahydroindolizine-1-carboxamide, 2-methyl-8-hydroxy-3-(2-fluoropyridin-3-yl)5,6,7,8-tetrahydroindolizine-1-carbonitrile, methyl 2-methyl-8-hydroxy-3-(2-fluoropyridin-3-yl)-5,6,7,8-tetrahydroindolizine-1-carboxylate, 1-acetyl-2-methyl-8-hydroxy-3-(2-fluoropyridin-3-yl)-5,6,7,8-tetrahydroindolizine, 2-trifluoromethyl-8-hydroxy-3-pyridin-3-yl-5,6,7,8-tetrahydroindolizine-1-carboxamide, 2-trifluoromethyl-8-hydroxy-3-pyridin-3-yl-5,6,7,8-tetrahydroindolizine-1-carbonitrile, methyl 2-trifluoromethyl-8-hydroxy-3-pyridin-3-yl-5,6,7,8-tetrahydroindolizine-1-carboxylate, 1-acetyl-2-trifluoromethyl-8-hydroxy-3-pyridin-3-yl-5,6,7,8-tetrahydroindolizine, 2-trifluoromethyl-8-hydroxy-3-(2-chloropyridin-3-yl)-5,6,7,8-tetrahydroindolizine-1-carboxamide, 2-trifluoromethyl-8-hydroxy-3-(2-chloropyridin-3-yl)-5,6,7,8-tetrahydroindolizine-1-carbonitrile, methyl 2-trifluoromethyl-8-hydroxy-3-(2-chloropyridin-3-yl)-5,6,7,8-tetrahydroindolizine-1-carboxylate, 1-acetyl-2-trifluoromethyl-8-hydroxy-3-(2-chloropyridin-3-yl)-5,6,7,8-tetrahydroindolizile, 2-trifluoromethyl-8-hydroxy-3-(2-fluoropyridin-3-yl)-5,6,7,8-tetrahydroindolizine-1-carboxamide, 2-trifluoromethyl-8-hydroxy-3-(2-fluoropyridin-3-yl)-5,6,7,8-tetrahydroindolizine-1-carbonitrile, methyl 2-trifluoromethyl-8-hydroxy-3-(2-fluoropyridin-3-yl)-5,6,7,8-tetrahydroindolizine-1-carboxylate, 1-acetyl-2-trifluoromethyl-8-hydroxy-3-(2-fluoropyridin-3-yl)-5,6,7,8-tetrahydroindolizine, methyl 2-chloro-3-pyridin-3-yl-5,6-dihydroindolizine-1-carboxylate, 1-acetyl-2-chloro-3-pyridin-3-yl-5,6-dihydroindolizine, 2-chloro-3-(2-chloropyridin-3-yl)-5,6-dihydroindolizine-1-carboxamide, 2-chloro-3-(2-chloropyridin-3-yl)-5,6-dihydroindolizine-1-carbonitrile, methyl 2-chloro-3-(2-chloropyridin-3-yl)-5,6-dihydroindolizine-1-carboxylate, 1-acetyl-2-chloro-3-(2-chloropyridin-3-yl)-5,6-dihydroindolizine, methyl 2-chloro-3-(2-fluoropyridin-3-yl)-5,6-dihydroindolizine-1-carboxylate, 1-acetyl-2-chloro-3-(2-fluoropyridin-3-yl)-5,6-dihydroindolizine, 2-chloro-7-methoxy-3-pyridin-3-yl-5,6-dihydroindolizine-1-carboxamide, 2-chloro-7-methoxy-3-pyridin-3-yl-5,6-dihydroindolizine-1-carbonitrile, methyl 2-chloro-7-methoxy-3-pyridin-3-yl-5,6-dihydroindolizine-1-carboxylate, 1-acetyl-2-chloro-7-methoxy-3-pyridin-3-yl-5,6-dihydroindolizine, 2-chloro-7-methoxy-3-(2-chloropyridin-3-yl)-5,6-dihydroindolizine-1-carboxamide, 2-chloro-7-methoxy-3-(2-chloropyridin-3-yl)-5,6-dihydroindolizine-1-carbonitrile, methyl 2-chloro-7-methoxy-3-(2-chloropyridin-3-yl)-5,6-dihydroindolizine-1-carboxylate, 1-acetyl-2-chloro-7-methoxy-3-(2-chloropyridin-3-yl)-5,6-dihydroindolizine, 2-chloro-7-methoxy-3-(2-fluoropyridin-3-yl)-5,6-dihydroindolizine-1-carboxamide, 2-chloro-7-methoxy-3-(2-fluoropyridin-3-yl)-5,6-dihydroindolizine-1-carbonitrile, methyl 2-chloro-7-methoxy-3-(2-fluoropyridin-3-yl)-5,6-dihydroindolizine-1-carboxilate, 1-acetyl-2-chloro-7-methoxy-3-(2-fluoropyridin-3-yl)-5,6-dihydroindolizine, 2,7-dichloro-3-pyridin-3-yl-5,6-dihydroindolizine-1-carboxamide, 2,7-dichloro-3-pyridin-3-yl-5,6-dihydroindolizine-1-carbonitrile, methyl 2,7-dichloro-3-(2-chloropyridin-3-yl)-5,6-dihydroindolizine-1-carboxylate, 1-acetyl-2,7-dichloro-3-(2-chloropyridin-3-yl)-5,6-dihydroindolizine, methyl 2,7-dichloro-3-(2-fluoropyridin-3-yl)-5,6-dihydroindolizine-1-carboxylate, 1-acetyl-2,7-dichloro-3-(2-fluoropyridin-3-yl)-5,6-dihydroindolizine, 2-cyano-3-pyridin-3-yl-5,6-dihydroindolizine-1-carboxamide, 2-cyano-3-pyridin-3-yl-5,6-dihydroindolizine-1-carbonitrile, methyl 2-cyano-3-pyridin-3-yl-5,6-dihydroindolizine-1-carboxylate, 1-acetyl-2-cyano-3-pyridin-3-yl-5,6-dihydroindolizine, 2-cyano-3-(2-chloropyridin-3-yl)-5,6-dihydroindolizine-1-carboxamide, 2-cyano-3-(2-chloropyridin-3-yl)-5,6-dihydroindolizine-1-carbonitrile, methyl 2-cyano-3-(2-chloropyridin-3-yl)-5,6-dihydroindolizine-1-carboxylate, 1-acetyl-2-cyano-3-(2-chloropyridin-3-yl)-5,6-dihydroindolizine, 2-cyano-3-(2-fluoropyridin-3-yl)-5,6-dihydroindolizine-1-carboxamide, 2-cyano-3-(2-fluoropyridin-3-yl)-5,6-dihydroindolizine-1-carbonitrile,
methyl 2-cyano-3-(2-fluoropyridin-3-yl)-5,6-dihydroindolizine-1-carboxylate,
1-acetyl-2-cyano-3-(2-fluoropyridin-3-yl)-5,6-dihydroindolizine,
2-methoxy-3-pyridin-3-yl-5,6-dihydroindolizine-1-carboxamide,
2-methoxy-3-pyridin-3-yl-5,6dihydroindolizine-1-carbonitrile,
methyl 2-methoxy-3-pyridin-3-yl-5,6-dihydroindolizine-1-carboxylate,
1-acetyl-2-methoxy-3-pyridin-3-yl-5,6-dihydroindolizine,
2-methoxy-3-(2-chloropyridin-3-yl)-5,6-dihydroindolizine-1-carboxamide,
2-methoxy-3-(2-chloropyridin-3-yl)-5,6-dihydroindolizine-1-carbonitrile,
methyl 2-methoxy-3-(2-chloropyridin-3-yl)-5,6-dihydroindolizine-1-carboxylate,
1-acetyl-2-methoxy-3-(2-chloropyridin-3-yl)-5,6-dihydroindolizine,
2-methoxy-3-(2-fluoropyridin-3-yl)-5,6-dihydroindolizine-1-carboxamide,
2-methoxy-3-(2-fluoropyridin-3-yl)-5,6-dihydroindolizine-1-carbonitrile,
methyl 2-methoxy-3-(2-fluoropyridin-3-yl)-5,6-dihydroindolizine-1-carboxylate,
1-acetyl-2-methoxy-3-(2-fluoropyridin-3-yl)-5,6-dihydroindolizine,
2-methyl-3-pyridin-3-yl-5,6-dihydroindolizine-1-carboxamide,
2-methyl-3-pyridin-3-yl-5,6-dihydroindolizine-1-carbonitrile,
methyl 2-methyl-3-pyridin-3-yl-5,6-dihydroindolizine-1-carboxylate,
1-acetyl-2-methyl-3-pyridin-3-yl-5,6-dihydroindolizine,
2-methyl-3-(2-chloropyridin-3-yl)-5,6-dihydroindolizine-1-carboxamide,
2-methyl-3-(2-chloropyridin-3-yl)-5,6-dihydroindolizine-1-carbonitrile,
methyl 2-methyl-3-(2-chloropyridin-3-yl)-5,6-dihydroindolizine-1-carboxylate,
1-acetyl-2-methyl-3-(2-chloropyridin-3-yl)-5,6dihydroindolizine,
2-methyl-3-(2-fluoropyridin-3-yl)-5,6-dihydroindolizine-1-carboxamide,
2-methyl-3-(2-fluoropyridin-3-yl)5,6-dihydroindolizine-1-carbonitrile,
methyl 2-methyl-3-(2-fluoropyridin-3-yl)-5,6-dihydroindolizine-1-carboxylate,
1-acetyl-2-methyl-3-(2-fluoropyridin-3-yl)-5,6-dihydroindolizine,
2-trifluoromethyl-3-pyridin-3-yl-5,6-dihydroindolizine-1-carboxamide,
2-trifluoromethyl-3-pyridin-3-yl-5,6-dihydroindolizine-1-carbonitrile,
methyl 2-trifluoromethyl-3-pyridin-3-yl-5,6-dihydroindolizine-1-carboxylate,
1-acetyl-2-trifluoromethyl-3-pyridin-3-yl-5,6-dihydroindolizine,
2-trifluoromethyl-3-(2-chloropyridin-3-yl)-5,6-dihydroindolizine-1-carboxamide,
2-trifluoromethyl-3-(2-chloropyridin-3-yl)-5,6-dihydroindolizine-1-carbonitrile,
methyl 2-trifluoromethyl-3-(2-chloropyridin-3-yl)-5,6-dihydroindolizine-1-carboxylate,
1-acetyl-2-trifluoromethyl-3-(2-chloropyridin-3-yl)-5,6-dihydroindolizine,
2-trifluoromethyl-3-(2-fluoropyridin-3-yl)-5,6-dihydroindolizine-1-carboxamide,
2-trifluoromethyl-3-(2-fluoropyridin-3-yl)5,6-dihydroindolizine-1-carbonitrile,
methyl 2-trifluoromethyl-3-(2-fluoropyridin-3-yil5,6-dihydroindolizine-1-carboxylate, and
1-acetyl-2-trifluoromethyl-3-(2-fluoropyridin-3-yl)5,6-dihydroindolizine.

3. A pyrrole compound according to claim 1, said compound having the following formula (VI):

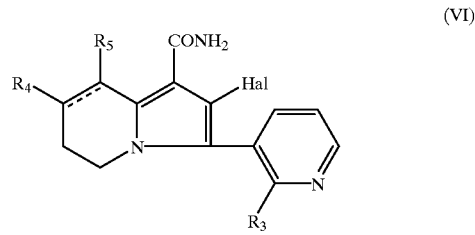

(VI)

in which:
Hal is a halogen atom, and
a) the bond - - - is a double bond,
R$_3$ is chosen from a hydrogen atom and halogen atoms,
R$_4$ is chosen from a hydrogen atom, halogen atoms, alkyloxy radicals, alkylthio radicals unsubstituted or substituted with carboxyl or alkylamino in which the alkyl parts optionally form, with the nitrogen atom to which they are attached, a 4- to 6-membered heterocycle which optionally has another heteroatom chosen from nitrogen, oxygen and sulphur, and 2-(1,3-dioxo-1,3-dihydroisoindol-2-yl)ethylsulphanyl, and
R$_5$ is a hydrogen atom,
or alternatively
b) the bond - - - is a single bond,
R$_3$ and R$_4$ are hydrogen atoms, and
R$_5$ is chosen from hydroxyl and alkyloxy radicals,
wherein said alkyl radicals are straight or branched and contain from 1 to 4 carbon atoms.

4. A pyrrole compound according to claim 3, wherein in said formula (VI):
Hal is a chlorine atom, and
a) the bond - - - is a double bond,
R$_3$ is chosen from a hydrogen atom and a chlorine atom,
R$_4$ is chosen from hydrogen, chlorine, methoxy, methylthio, 2-(1,3-dioxo-1,3-dihydroisoindol-2-yl) ethylsulphanyl, and 2-aminoethylsulphanyl, and
R$_5$ is hydrogen,
or alternatively
b) the bond - - - is a single bond,
R$_3$ and R$_4$ are hydrogen, and
R$_5$ is chosen from hydroxyl and methoxy.

5. A pyrrole compound according to claim 1, wherein said pyrrole compound is 2-chloro-8-hydroxy-3-(pyridin-3-yl)5, 6,7,8-tetrahydroindolizine-1-carboxamide.

6. A pyrrole compound according to claim 1, wherein said pyrrole compound is 2-chloro-8-methoxy-3-(pyridin-3-yl)-5,6,7,8-tetrahydroindolizine-1-carboxamide.

7. A pyrrole compound according to claim 1, wherein said pyrrole compound is 2-chloro-7-methoxy-3-(pyridin-3-yl)-5,6-dihydroindolizine-1-carboxamide.

8. A pyrrole compound according to claim 1, wherein said pyrrole compound is 2,7-dichloro-3-(pyridin-3-yl)-5,6-dihydroindolizine-1-carboxamide.

9. A process for making a pyrrole compound having the following formula (I), its stereoisomer, salt, or a mixture thereof:

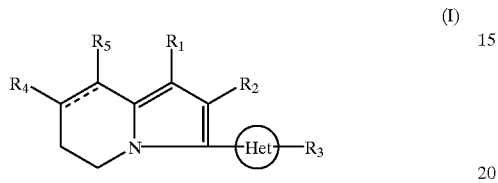
(I)

in which
$R_1$ is chosen from carboxamide, cyano, carboxyl, alkyloxycarbonyl, acetyl and imidazolylcarbonyl radicals,
$R_3$ is chosen from a hydrogen atom, halogen atoms, alkyl radicals and hydroxyl radicals, and
Het is chosen from pyridyl, pyridyl N-oxide and thiazolyl radicals, and
a) the bond - - - is a single bond,
$R_2$ is chosen from a hydrogen atom, halogen atoms, cyano, alkyl, alkyloxy and trihalomethyl radicals,
$R_4$ is a hydrogen atom, and
$R_5$ is chosen from hydroxyl, alkyloxy, amino and haloacylamino radicals,
or alternatively
b) the bond - - - is a double bond, and
$R_2$ is chosen from a hydrogen atom, halogen atoms, cyano, alkyl, alkyloxy, alkenyl and trihalomethyl radicals,
$R_4$ is chosen from a hydrogen atom, halogen atoms, alkyloxy radicals and alkylthio radicals which are unsubstituted or substituted with carboxyl, alkyloxycarbonyl, amino, alkylamino or dialkylamino in which the alkyl parts optionally form, with the nitrogen atom to which they are attached, phthalimido or a 4- to 6-membered heterocycle which optionally has another heteroatom chosen from nitrogen, oxygen and sulphur, and
$R_5$ is a hydrogen atom,
wherein $R_2$ is not chlorine when simultaneously $R_4$ and $R_5$ are hydrogen, and when $R_1$ is cyano or carboxamido, and Het-$R_3$ is 3-pyridyl optionally substituted with fluorine at the 2 position, or alternatively when simultaneously $R_4$ is halogen, $R_5$ is hydrogen, and when $R_1$ is cyano or carboxamido and Het-$R_3$ is 3-pyridyl substituted with methyl, chlorine or fluorine at the 2 position or when $R_1$ is alkyloxycarbonyl or acetyl and when Het-$R_3$ is 3-pyridyl,
and wherein said alkyl radicals are straight or branched and contain from 1 to 4 carbon atoms and said acyl and alkenyl radicals are straight or branched and contain from 2 to 4 carbon atoms,
said process comprising preparing a nitrile intermediate of the following formula (IV):

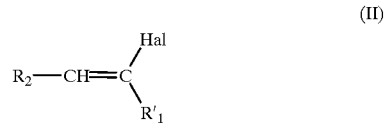
(IV)

in which Het, $R_2$ and $R_3$ are defined as above, by reacting an acrylic derivative of the following formula (II):

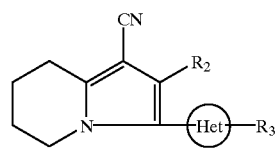
(II)

in which $R_2$ is chosen from a hydrogen atom and cyano, alkyl, alkyloxy and trihalomethyl radicals, $R'_1$ is chosen from cyano and alkyloxycarbonyl radicals, and Hal is a halogen atom,
with an acid of the following formula (III):

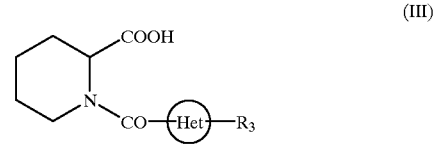
(III)

in which Het and $R_3$ are defined as above,
introducing said double bond, said radicals $R_4$ and $R_5$, and/or said radical $R_2$, and
optionally converting said nitrile intermediate to an amide, an acid, an ester, an imidazole-containing radical or an acetyl radical,
or optionally converting an ester radical to an acid, an imidazole-containing radical or an acetyl radical, and
optionally separating the resulting compound into its stereoisomeric forms and/or converting the resulting compound to a salt.

10. A pharmaceutical composition comprising an effective amount of at least one pyrrole compound of the following formula (I):

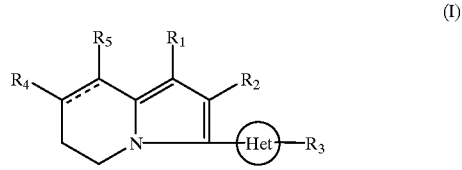
(I)

in which
a) the bond - - - is a single bond,
$R_1$ is chosen from carboxamide, cyano, carboxyl, alkyloxycarbonyl, acetyl and imidazolylcarbonyl radicals,
$R_3$ is chosen from a hydrogen atom, halogen atoms, alkyl radicals and hydroxyl radicals, and
Het is chosen from pyridyl, pyridyl N-oxide and thiazolyl radicals, and $R_2$ is chosen from a hydrogen atom, halogen atoms, cyano, alkyl, alkyloxy and trihalomethyl radicals, $R_4$ is a hydrogen atom, and $R_5$ is chosen from hydroxyl, alkyloxy, amino and haloacylamino radicals, or alternatively b) the bond - - - is a double bond, and $R_2$ is chosen from a hydrogen atom, halogen atoms, cyano, alkyl, alkyloxy, alkenyl and trihalomethyl radicals, $R_4$ is chosen from alkyloxy radicals and alkylthio radicals which are unsubstituted or substituted with carboxyl, alkyloxycarbonyl, amino, alkylamino or dialkylamino in which the alkyl parts optionally form, with the nitrogen atom to which they are attached, phthalimido or a 4- to 6-membered heterocyde which optionally has another heteroatom chosen from nitrogen, oxygen and sulphur, $R_5$ is a hydrogen atom, $R_1$ is chosen from carboxamido, cyano, carboxyl, alkyloxycarbonyl, acetyl and imidazolylcarbonyl radicals, $R_3$ is chosen from a hydrogen atom, halogen atoms, alkyl radicals and hydroxyl radicals, and Het is chosen from pyridyl, pyridyl N-oxide and thiazolyl radicals, or $R_2$ is chosen form a hydrogen atom, a bromine atom, an iodine atom, a fluorine atom, cyano, alkyl, alkyloxy, alkenyl, and trihalomethyl radicals, $R_4$ is chosen from a hydrogen atom and halogen atoms, $R_5$ is a hydrogen atom, $R_1$ is chosen from carboxamido, cyano, carboxyl, alkyloxycarbonyl, acetyl and imidazolylcarbonyl radicals, $R_3$ is chosen from a hydrogen atom, halogen atoms, alkyl radicals and hydroxyl radicals, and Het is chosen from pyridyl, pyridyl N-oxide and thiazolyl radicals, or $R_2$ is a chlorine atom, $R_4$ is chosen from a hydrogen atom and halogen atoms, $R_5$ is a hydrogen atom, $R_1$ is chosen from carboxyl and imidazolylcarbonyl radicals, $R_3$ is chosen from a hydrogen atom, halogen atoms, alkyl radicals and hydroxyl radicals, and Het is chosen from pyridyl, pyridyl N-oxide and thiazolyl radicals, or $R_2$ is a chlorine atom, $R_4$ is chosen from a hydrogen atom and halogen atoms, $R_5$ is a hydrogen atom, $R_1$ is chosen from carboxamido, cyano, alkyloxycarbonyl and acetyl radicals, and $R_3$ is chosen from a hydrogen atom, halogen atoms, alkyl radicals and hydroxyl radicals, and Het is chosen from pyridyl-2, pyridyl-4, pyridyl N-oxide and thiazolyl radicals, or $R_3$ is chosen from a bromine atom, an iodine atom, and a hydroxyl radical, and Het is pyridyl-3, wherein said alkyl radicals are straight or branched and contain from 1 to 4 carbon atoms and said acyl and alkenyl radicals are straight or branched and contain from 2 to 4 carbon atoms, together with a pharmaceutically acceptable carrier.

11. A process according to claim 9, wherein said Hal is chlorine.

\* \* \* \* \*